United States Patent [19]

Kusama et al.

[11] Patent Number: 5,134,230
[45] Date of Patent: Jul. 28, 1992

[54] 2-DEOXY-2-AMINOGLUCOPYRANOSIDE DERIVATIVES

[75] Inventors: Tsuneo Kusama; Tsunehiko Soga, both of Tokyo; Tetsuo Shiba, Osaka, all of Japan

[73] Assignee: Daiichi Pharmaceutical Co., Ltd., Tokyo, Japan

[21] Appl. No.: 614,417

[22] Filed: Jan. 18, 1991

Related U.S. Application Data

[62] Division of Ser. No. 162,932, Mar. 2, 1988, Pat. No. 5,006,647.

[51] Int. Cl.$^5$ .............. C07H 11/04; C07H 13/00; C07H 5/04; C07H 5/06
[52] U.S. Cl. .................. 536/117; 536/120; 536/55.2; 536/22; 536/17.9; 536/17.2; 536/18.2; 536/4.1; 536/116; 536/53; 536/18.7; 536/124
[58] Field of Search .......... 536/117, 120, 17.2, 536/17.9, 22, 55.2

[56] References Cited

U.S. PATENT DOCUMENTS 4,693,998 9/1987 Lefrancier et al. ............ 536/55.2

OTHER PUBLICATIONS

Chemical Abstracts, vol. 112, No. 21, issued 1990, May 21 (Columbus, Ohio, U.S.A.) Kusama et al., 'Preparation of amino Disaccharide as Antitumor Agents', see p. 775, column 2, the abstract no. 198980S, Eur. Pat. Appl. EP 330,715, Sep. 6, 1989, Appl. 88/103,185, Mar. 2, 1988; 81 pp.
Chemical Abstracts, vol. 110, no. 15, issued 1989, Apr. 10 (Columbus, Ohio, U.S.A.) Nichima et al., 'Preparation of 6-0-(B-D-glucoaminyl)-α-D-glucoamine derivatives as antitumor agents, see p. 757, column 2, the abstract no. 135648c, Jpn. Kokai Tokyo Koho JP 63,183,594 [88,183,594], Jul. 28, 1988, JP Appl. 86/206,537, Sep. 2, 1986; 28 pp.
Chemical Abstracts, vol. 112, No. 9, issued 1990, Feb. 26 (Columbus, Ohio, U.S.A.), Kusama et al., 'Preparation and Testing of N$_2$O-acyldiglucosamine Phosphate as Antitumor Agents' see p. 867, column 2, the abstract no. 77859a, S. African ZA 88.01,430, Dec. 28, 1988, Appl. 88/1430, Feb. 29, 1988; 117 pp.
Chemical Abstracts, vol. 112, No. 11, issued Mar. 12, 1990, (Columbus, Ohio, U.S.A.) Nichima et al., 'Preparation of 6-0-(β-D-Glucosaminyl)glucosamine Derivatives as Antitumor Agents', see page 812, column 1, the abstract no. 99142p, Jpn. Kokai Tokkyo Koho JP 01,221,387 [89,221, 387], Sep. 4, 1989, Appl. 88/47,247, Feb. 29, 1988; 43 pp.
Chemical Abstracts, vol. 113, No. 17, issued Oct. 22, 1990 (Columbus, Ohio, U.S.A.) Shiba et al., 'Preparation of 6-O-(β-D-glucosaminyl)-D-glucosamine phosphate Derivatives as Antitumor Agents' see p. 834, column 1, the abstract no. 752973; Pat. Specif. (Aug.) AU 595987, Apr. 12, 1990, Appl. 88/12,541, Mar. 1, 1988; 121 pp.
Chemical Abstracts, vol. 97, No. 11, issued 1982 (Columbus, Ohio, U.S.A.) Van Boeckel et al., "Chemical Synthesis of Diphospharylated Lipid A Derivatives" see page 810, colunmn 1, the abstract no. 92667b, Tetrahedron Letters, 1982, 23(18), 1951-1954 (Eng.).
Chemical Abstracts, vol. 100, No. 15, issued 1984 (Columbus, Ohio, U.S.A.), Van Boeckel et al., "Synthesis of Two Diphospharylated Lipid A Derivatives containing alpha-or beta-anomeric phosphates" see p. 632, column 2, the abstract no. 121493e, Recl.: J. R. Neth. Chem. Soc. 1983, 102 (10), 438-449 (Eng.).
Chemical Abstracts, vol. 109, no. 15, issued 1988, Oct. 10 (Columbus, Ohio, U.S.A.), Wong et al., "Synthesis of D-Galactosamine Derivatives and Binding Studies using Isolated Rat Hepatocytes" see page 744, column 2, the abstract no. 129528b, Carbohydrate Res. 1987, 170(1), 27-46 (Eng.).

*Primary Examiner*—Johnnie R. Brown
*Assistant Examiner*—Everett White
*Attorney, Agent, or Firm*—Sughrue, Mion, Zinn, Macpeak & Seas

[57] ABSTRACT

A disaccharide compound represented by formula (I):

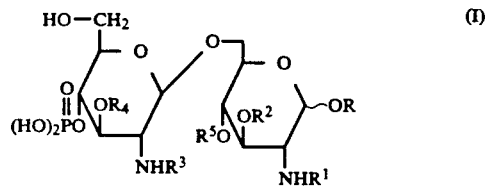

wherein R, $R^1$, $R^2$, $R^3$, $R^4$, and $R^5$ are as defined in the specification and a salt thereof are disclosed. The compound exhibits excellent antitumor activity and low toxicity and is useful as an antitumor agent.

15 Claims, No Drawings

2-DEOXY-2-AMINOGLUCOPYRANOSIDE DERIVATIVES

This is a divisional of application Ser. No. 07/162,932 filed Mar. 2, 1988, now U.S. Pat. No. 5,006,647.

FIELD OF THE INVENTION

This invention relates to novel disaccharide derivatives and salts thereof which exhibits excellent antitumor activity and low toxicity, and is useful as an antitumor agent.

BACKGROUND OF THE INVENTION

Natural lipid A has mitogenic activity, i.e., an activity to stimulate lymphocytes to cause blast transformation, which accelerates increase of lymphatic cells thereby to enhance immunity, an activity to derive a tumor necrosis factor, and the like, and is, therefore, promising as a treating and prophylactic agent for many diseases caused by a reduction of immune function, such as various infectious diseases, or antitumor agents.

Known derivatives of natural lipid A include those described in Japanese Patent Application (OPI) Nos. 48497/84, 53295/86, and 227586/86 (the term "OPI" as used herein means "unexamined published Japanese patent application"). Among them, 2-deoxy-6-O-(2-deoxy-2-[(R)-3-dodecanoyloxytetradecanoylamino]-4-O-phosphono-3-O-[(R)-4-tetradecanoyloxytetradecanoyl]-β-D-glucopyranosyl)-3-O-[(R)-3-hydroxytetradecanoyl]-2-[(R)-3-hydroxytetradecanoylamino]-1-O-phosphono-α-D-glucopyranose disclosed in Japanese Patent Application (OPI) No. 53295/86 (hereinafter referred to as Compound A) is known to have physiological activities equal to or even higher than natural lipid A as reported in *Eur. J. Biochem.*, Vol. 148, 1–5 (1985). Compound A, however, is of low practical use due to high toxicity similar to natural lipid A. The above-described known compounds other than Compound A are also unsatisfactory for practical use in terms of toxicity or antitumor activity. It has been keenly demanded, therefore to develop compounds exhibiting useful physiological properties with reduced toxicity.

SUMMARY OF THE INVENTION

The inventors have conducted extensive investigations to develop a compound having useful physiological activities and low toxicity and, as a result, reached the present invention.

This invention relates to compounds represented by formula (I):

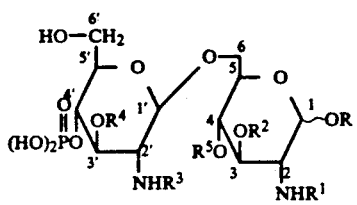

wherein R represents a phosphono group, $ZR^6$ or

wherein
$Z$, $Z^1$, and $Z^2$ each represents an alkylene group having from 1 to 6 carbon atoms, and $R^6$ represents a carboxyl group or a phosphonoxy group;

$R^1$, $R^2$, $R^3$, and $R^4$ each represents $-COR^7$, $-COZ^3R^8$,

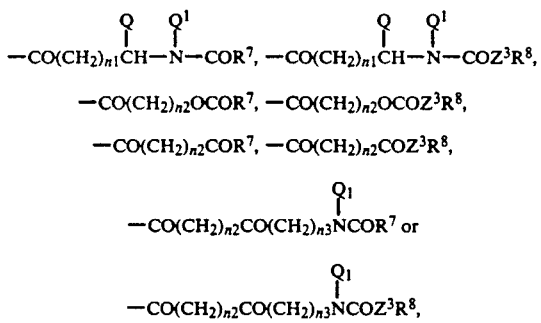

wherein
$R^7$ represents an alkyl group having from 1 to 30 carbon atoms which may be substituted with one or more hydroxyl groups, $Z^3$ represents an alkylene group having from 1 to 9 carbon atoms, $R^8$ represents a cycloalkyl group having from 3 to 12 carbon atoms which may be substituted with one or more hydroxyl groups, $Q$ represents a hydrogen atom, an alkyl group having from 1 to 6 carbon atoms, $-CONH_2$, $-COOH$ or $-CH_2OH$, $Q_1$ represents a hydrogen atom or an alkyl group having from 1 to 20 carbon atoms, n1 represents 0 or an integer of from 1 to 10, and n2 and n3 each represents an integer of from 1 to 20; and $R^5$ represents a hydrogen atom, a phosphono group or $-CO(CH_2)_mCOOH$, wherein m represents 0 or an integer of from to 6;

provided that a combination wherein R is a phosphono group, $R^5$ is a hydrogen atom, and $R^1$, $R^2$, $R^3$, and $R^4$ each is $-COR^7$ is excluded, and a salt thereof.

The compounds represented by formula (I) and salts thereof exhibit excellent antitumor activity and low toxicity and are useful as antitumor agents.

DETAILED DESCRIPTION OF THE INVENTION

The term "alkylene group" as used herein means a methylene group, a polymethylene group, or a methylene or polymethylene group substituted with an alkyl group having from 1 to 6 carbon atoms. Specific examples of the alkylene group are methylene, ethylene, propylene, trimethylene, ethylethylene, tetramethylene, 2-methyltetramethylene, 2,3-dimethyltetramethylene, 2-ethyl-3-methylpentamethylene and octamethylene groups, etc. In formula (I), the alkylene group as represented by Z, $Z^1$, $Z^2$ or $Z^3$ preferably contains from 1 to 4 carbon atoms.

The term "alkyl group" as used herein means a straight or branched chain alkyl group and includes, for example, methyl, ethyl, propyl, t-butyl, hexyl, nonyl, decyl, 3-ethylundecyl, 2-ethyl-4-methyltridecyl, tetradecyl, nonadecyl, tetraeicosyl, 2-ethyl-5-propyltetraeicosyl, and octaeicosyl groups. The alkyl group as represented by $R^7$ preferably contains from 5 to 20 carbon atoms.

The term "cycloalkyl group" as used herein includes, for example, cyclobutyl, cycloheptyl, cyclohexyl, cycloheptyl, cyclodecyl, and cyclododecyl groups, and preferably those having from 5 to 8 carbon atoms.

In formula (I), n1 preferably represents 0 or an integer of from 1 to 5, and n2 and n3 each preferably represents an integer of from 1 to 6.

The compounds of formula (I) include α- and β-isomers due to the substituent OR, both of which and a mixture of which fall within the scope of the present invention. Further, the compounds of formula (I) embrace optical isomers due to various substituents, and such optical isomers and mixtures thereof also fall within the scope of the present invention.

The salts of the compounds of formula (I) includes salts formed between the phosphono group or carboxyl group thereof and organic amines, e.g., triethylamine, pyridine, N-methylamine, N-methylglucamine, etc., or inorganic bases, e.g., ammonia, sodium, potassium, calcium, magnesium, etc.

Of the compounds of formula (I), preferred are those wherein R represents $ZR^6$ or

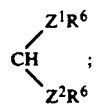

$R^1$, $R^2$, $R^3$, and $R^4$ each represents —$COR^7$, —$COZ^3R^8$,

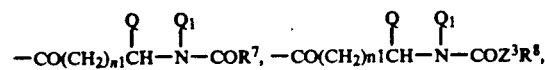

—$CO(CH_2)_{n2}COR^7$ or —$CO(CH_2)_{n2}COZ^3R^8$. More preferred are those wherein R represents $ZOPO(OH)_2$, and $R^1$, $R^2$, $R^3$, and $R^4$ each represents —$COR^7$ or

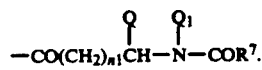

The compounds according to the present invention can be prepared through various reaction routes. One example of the processes is illustrated below.

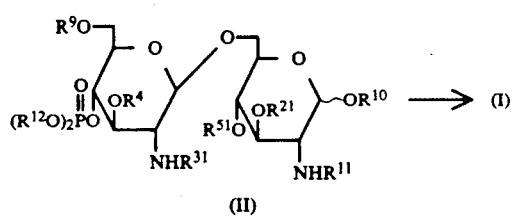

wherein $R^9$ represents a hydrogen atom or a hydroxyl-protective group (i.e., a protective group for the hydroxyl group) which can be removed by catalytic reduction or the like; $R^{10}$ represents

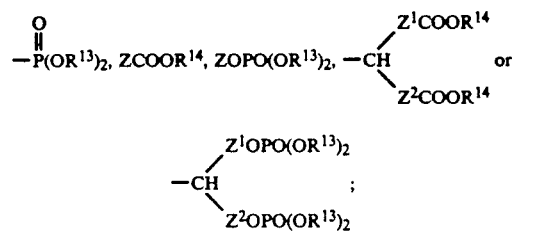

$R^{11}$, $R^{21}$, and $R^{31}$ each represents —$COR^{71}$, —$COZ^3R^{81}$,

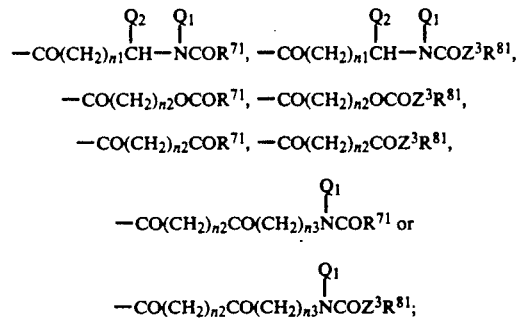

$R^{51}$ represents a hydrogen atom, —$CO(CH_2)_mCOOR^{16}$ or $PO(OR^{15})_2$, wherein $R^{12}$ and $R^{13}$ represents a phosphono-protective group which can be removed by catalytic reduction; $R^{14}$ represents a carboxyl-protective group which can be removed by catalytic reduction; $R^{71}$ represents an alkyl group having from 1 to 30 carbon atoms which may be substituted with one or more hydroxyl groups protected with a hydroxyl-protective group; $R^{81}$ represents a cycloalkyl group having from 3 to 12 carbon atoms which may be substituted with one or more hydroxyl groups protected with a hydroxyl-protective group; $Q_2$ represents a hydrogen atom, an alkyl group having from 1 to 6 carbon atoms, —$CONH_2$, —$COOR^{16}$ or —$CH_2$—O—$R^{91}$, wherein $R^{16}$ represents a carboxyl-protective group which can be removed by catalytic reduction; $R^{15}$ represents a phosphono-protective group which can be removed by catalytic reduction; and $R^{91}$ represents a hydroxyl-protective group which can be removed by catalytic reduction; and Z, $Z^1$, $Z^2$, $Z^3$, Q, n1, n2, n3, and m are as defined above.

The carboxyl-protective group which can be removed by catalytic reduction includes a benzyl group, etc., which may be substituted with a halogen atom, a nitro group, a lower alkoxy group, etc. The phosphono-protective group which can be removed by catalytic reduction includes a phenyl group, a benzyl group, etc., each of which may be substituted with a halogen atom, a nitro group, a lower alkoxy group, etc. The hydroxyl-protective group includes those removable by catalytic reduction, such as a benzyl group, etc., which may be substituted with a halogen atom, a nitro group, a lower alkoxy group, etc., a trichloroethoxycarbonyl group, a trichloro-t-butoxycarbonyl group, etc.

According to the above-described process, the compound of formula (II) is catalytically reduced in an inert solvent, e.g., tetrahydrofuran, methanol, ethanol, acetic acid, water, a mixture of these solvents, etc., in a hydrogen gas atmosphere in the presence of a catalyst, such as palladium black, palladium-on-carbon, platinum dioxide, etc., to thereby remove the protective groups. If desired, the product may be purified by silica gel chromatography or the like technique. The reduction reaction can usually be carried out at a temperature of from room temperature (0° to 30° C.) to 60° C. for a period of from 1 to 12 hours. The amounts of the solvent and catalyst to be used are not particularly limited.

In cases of using the compound of formula (II) wherein $R^{11}$, $R^{21}$ or $R^{31}$ contains therein a hydroxyl-protective group, such a protective group is preferably the one removable by catalytic reduction.

The salt of the compound of formula (I) can be obtained by adding a necessary amount of a base to the compound, followed by sedimentation, freeze-drying or the like means.

The process for preparing the starting compound represented by formula (II) can be selected appropriately depending on the kind of the substituents $R^{10}$ and $R^{51}$ as illustrated below.

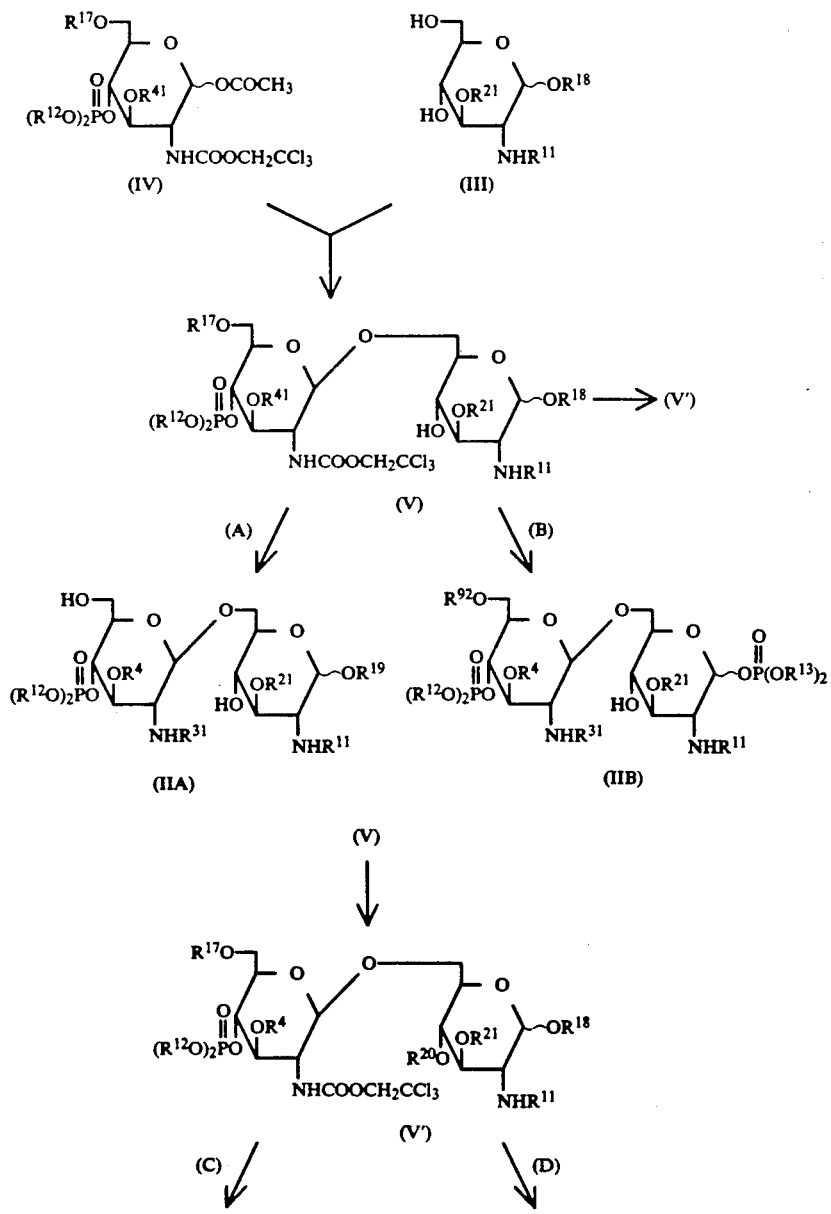

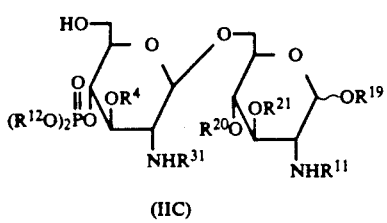

(IIC)

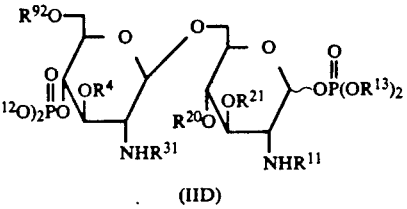

(IID)

wherein $R^{18}$ represents an allyl group, $ZCOOR^{14}$, $ZOPO(OR^{13})_2$,

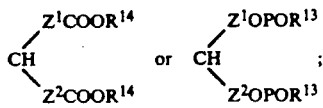

$R^{17}$ represents a hydroxyl-protective group; $R^{41}$ represents $-COR^{71}$, $-COZ^3R^{81}$,

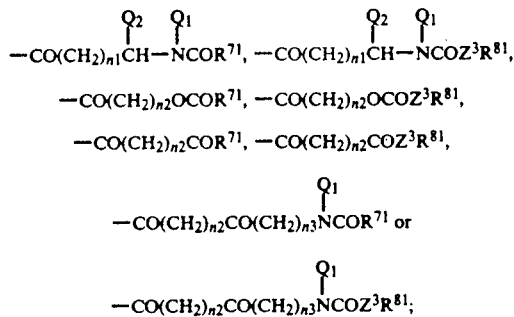

$R^{19}$ represents $ZCOOR^{14}$, $ZOPO(OR^{13})_2$,

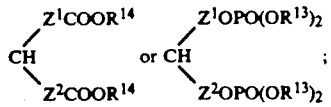

$R^{20}$ represents $-CO(CH_2)COOR^{16}$ or $PO(OR^{15})_2$; $R^{92}$ represents a hydroxyl-protective group removable by catalytic reduction; and $R^{11}$, $R^{21}$, $R^{31}$, $R^{12}$, $R^{13}$, $R^{14}$, $R^{15}$, $R^{16}$, $R^{71}$, $R^{81}$, Z, $Z^1$, $Z^2$, $Z^3$, n1, $Q_2$, $Q_1$, n2, n3, and m are as defined above More specifically, the compound of formula (IV) is dissolved in an inert solvent (e.g., methylene chloride, acetic acid, etc., either alone or combinations thereof) containing hydrogen bromide gas and allowed to react at 0° C. to room temperature for several tens minutes to about 24 hours to thereby substitute the acetyl group at the 1-position of the sugar moiety by a bromine atom. The resulting bromo-substituted compound is dissolved in a dried solvent, preferably, methylene chloride, chloroform, etc., and then condensed with the compound of formula (III) in the presence of either one or more of mercury (II) cyanide, mercury bromide, silver carbonate, silver oxide, silver perchlorate, mercury (II) nitrate, etc. and in the presence of a dehydrating agent, e.g., anhydrous calcium sulfate, etc., at a temperature of from room temperature to the reflux temperature for a period of several hours to 2 days, thereby to obtain the compound of formula (V).

The resulting compound was then reacted with a compound of formula $X-R^{20}$, wherein X represents a halogen atom, in an organic solvent, e.g., methylene chloride, chloroform, acetonitrile, tetrahydrofuran, etc., in the presence of an organic base, e.g., pyridine, 4-dimethylamino pyridine, triethylamine, etc., or reacted with a compound of the formula $HO-R^{20}$ and a catalyst such as dicyclohexylcarbodiimide in the presence of 4-dimethylaminopyridine to obtain the compound of formula (V').

The compounds represented by formulae (IIA) to (IID), i.e., the starting compounds of formula (II), can then be synthesized from the thus obtained compounds of formula (V) and (V') through the following reaction routes (A) to (D).

Reaction Route (A)

A compound of formula (V) wherein $R^{18}$ or $R^{19}$ is dissolved or suspended in acetic acid, and zinc powder is added thereto to effect reaction, thereby removing the amino-protective group at the 2'-position and $R^{17}$. The resulting compound freed from the protective group is then condensed with the compound of formula $R^{31}$-OH according to a process commonly employed in peptide synthesis to prepare the compound of formula (IIA).

The removal of the protective group is usually Performed at room temperature for several tens of minutes to 24 hours. The condensation reaction can be effected by a carbodiimide method, the Eintopf method, an active ester method, and the like.

In the above-described reaction for removal of protective groups, a trichloroethoxycarbonyl group or a trichloro-t-butoxycarbonyl group is preferred as $R^{17}$, i.e., a protective group for a hydroxyl group. When $R^{41}$ has a hydroxyl-protective group in the molecule thereof, the same groups are preferred as the hydroxyl-protective group.

Reaction Route (B)

A compound of formula (V) wherein $R^{18}$ is an allyl group is treated in the same manner as in Reaction Route (A) to remove and then to bond $R^{31}$ to the 2'-positioned amino group. After protecting the 6'-positioned hydroxyl group with a protective group removable by catalytic reduction, the compound is reacted with an iridium complex, e.g., 1,5-cyclooctadienebis(-methyldiphenylphosphine)-iridium hexafluorophosphate, etc., followed by hydrolysis to remove the allyl group. The resulting compound is then reacted with

to obtain the compound of formula (IIB).

Protection of the 6'-positioned hydroxyl group can be carried out, for example, by reacting with benzyloxymethyl chloride in an organic solvent, e.g., anhydrous chloroform, anhydrous methylene chloride, etc., in the presence of an organic base, e.g., pyridine, diisopropylethylamine, etc., at room temperature for 1 to 2 days. The protection may also be effected by using benzyl trichloroacetimidate in the presence of trifluoromethanesulfonic acid at around 0° C.

Removal of the allyl group is usually carried out by reacting with the above-described iridium complex in an organic solvent, e.g., methylene chloride, chloroform, tetrahydrofuran, etc., at about 50° C. for a period of from 10 minutes to 3 hours and then adding water and iodine to the reaction mixture to effect hydrolysis at room temperature for about 5 to 30 minutes.

The reaction between the allyl-free compound and

is usually conducted in an anhydrous aprotic solvent, e.g., anhydrous tetrahydrofuran, in the presence of butyl lithium at a temperature of from −70° C. to 50° C. for several tens of minutes.

Reaction Route (C)

The compound of formula (IIC) can be prepared by subjecting a compound of formula (V') to the same reactions of Reaction Route (A).

Reaction Route (D)

The compound of formula (IID) can be prepared by subjecting the compound of formula (V') to the same reactions of Reaction Route (B).

The compound of formula (IV) used as a starting material in the above-illustrated process can be synthesized according to known processes or the process disclosed in Japanese Patent Application (OPI) No. 53295/86.

The compound of formula (III), the other starting material in the process, can be prepared by Reaction Route (a) or (b) shown below, selected according to the kind of the substituent $R^{18}$.

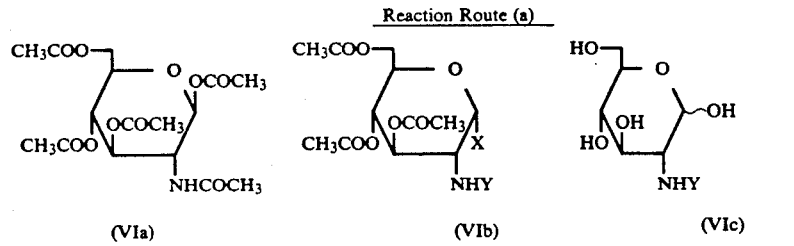

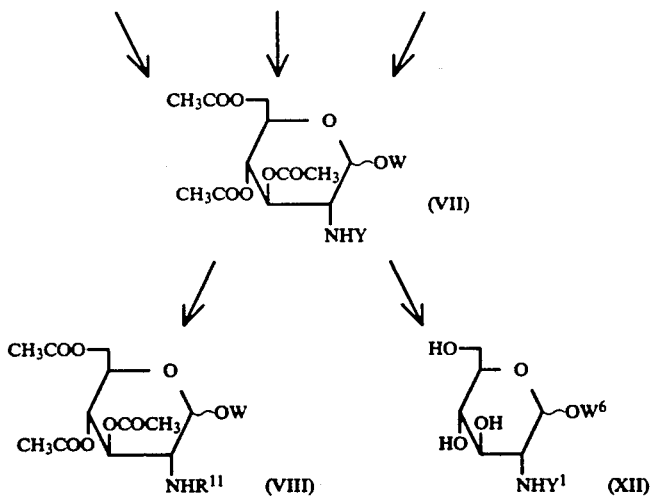

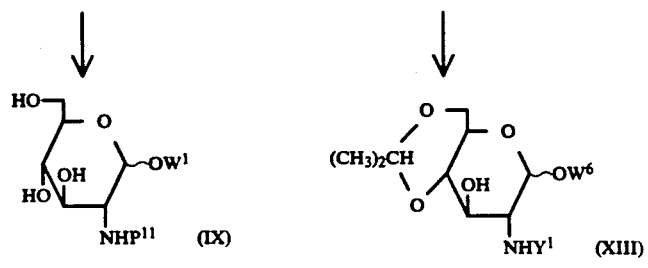

-continued

Reaction Route (a)

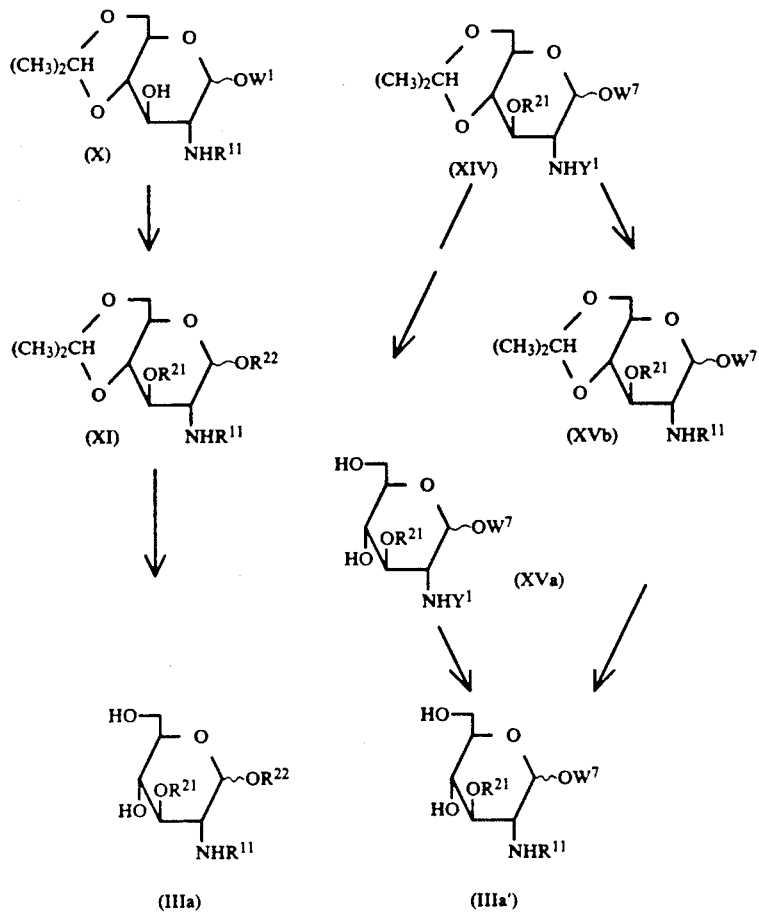

wherein X represents a halogen atom; Y represents a lower acyl group, a trichloroethoxycarbonyl group or a trichloro-t-butoxycarbonyl group; W represents ZOW$^2$, ZCOOW$^2$,

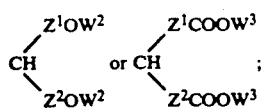

W$^1$ represents ZOW$^4$, ZCOOR$^{13}$,

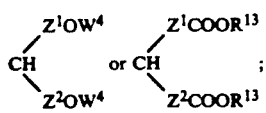

R$^{22}$ represents ZOPO(OR$^{13}$)$_2$, ZCOOR$^{14}$,

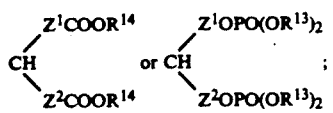

W$^6$ represents ZOH or

W$^7$ represents ZOPO(OR$^{13}$)$_2$ or

Y$^1$ represents a trichloroethoxycarbonyl group or a trichloro-t-butoxycarbonyl group; W$^2$ represents an acetyl group, a benzoyl group, a benzyl group or a p-chlorobenzyl group; W$^3$ represents an alkyl group having from to 6 carbon atoms or a carboxyl-protective group removable by catalytic reduction; W$^4$ represents a hydrogen atom, a benzyl group or a p-chlorobenzyl group; and R$^{11}$, R$^{21}$, R$^{13}$, R$^{14}$, Z, Z$^1$, and Z$^2$ are as defined above.

The compound of formula (VII) can be prepared by reacting a compound of formula. (VIa) with a compound of formula WOH in the presence of a Lewis acid or condensing a compound of formula (VIb) with the compound WOH in the presence of mercury (II) cyanide, silver carbonate, mercury bromide, silver perchlorate or mercury (II) nitrate, or a mixture thereof. The compound of formula (VII) wherein W is a ZO-acetyl group can be obtained by reacting a compound of formula (VIc) with a compound of formula HOZOH in the presence of hydrogen chloride, p-toluenesulfonic acid, etc., followed by acetylation.

The compound of formula (VII) wherein Y is a lower acyl group is treated with a Meerwein reagent, or the compound of formula (VII) wherein Y is a trichloroethoxycarbonyl or trichloro-t-butoxycarbonyl group is treated with zinc powder in the presence of hydrochloric acid, acetic acid, etc. to thereby remove the protective group for the 2-positioned amino group. The resulting compound is then condensed with a compound of formula $R^{11}OH$ according to an acid chloride method, a carbodiimide method, the Eintopf method or an active ester method to prepare the compound of formula (VIII).

The compound of formula (VIII wherein W is ZCOO-alkyl or

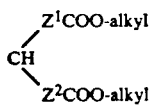

is hydrolyzed with sodium hydroxide, etc., to remove the acyl and alkyl groups, and the resulting compound is reacted with a compound of formula $X-R^{14}$ in the presence of an organic amine, e.g., triethylamine, to prepare the compound of formula (IX). The compound of formula (VIII) wherein W has other meanings is hydrolyzed with aqueous ammonia, etc., to obtain the compound of formula (IX).

The hydroxyl groups at the 4- and 6-positions of the compound of formula (IX) are protected using isopropylidene to obtain the compound of formula (X).

The compound of formula (X) wherein $W^1$ is a Z—O-benzyl or ZO-p-chlorobenzyl group is condensed with a compound of formula $R^{21}$-OH and then the resulting compound is catalytically reduced to the compound wherein $W^1$ is ZOH. The resulting compound is reacted with a compound of formula $X-PO(OR^{13})_2$ in the presence of an organic amine, e.g., triethylamine, 4-dimethylaminopyridine, pyridine, etc., to prepare the compound of formula (XI).

The compound of formula (X) wherein $W^1$ is $ZCOOR^{14}$ or

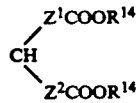

is condensed with the compound of formula $R^{21}$—OH to prepare the compound of formula (XI).

The compound of formula (IIIa) can be obtained by hydrolyzing the thus prepared compound of formula (XI) in aqueous acetic acid, e.g., a 50 to 90% by weight aqueous solution of acetic acid, or treating the compound with p-toluenesulfonic acid in methanol, ethanol, water or a mixture thereof.

The compound of formula (IIIa) wherein $R^{22}$ is $ZOPO(OR^{13})_2$ or

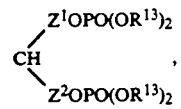

i.e., the compound of formula (IIIa'), can be prepared as follows.

The compound of formula (VII) wherein W is ZO-acetyl, ZO-benzoyl,

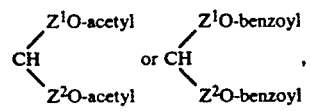

and Y is a trichloroethoxycarbonyl or trichloro-t-butoxycarbonyl group is treated with aqueous ammonia to obtain the compound of formula (XII), which is then protected with isopropylidene to obtain the compound of formula (XIII). The resulting compound is condensed with the compound of formula $XPO(OR^{13})_2$ and then with the compound of formula $R^{21}OH$ to prepare the compound of formula (XIV). The isopropylidene is removed from the resulting compound in the same manner as described above to prepare the compound of formula (XVa). $Y^1$ of the compound of formula (XVa) is removed in the same manner as described above, and the resulting compound is then condensed with the compound of formula $R^{11}OH$ to obtain the compound of formula (IIIa'). The compound of formula (XVb) can be prepared by removing $Y^1$ from the compound of formula (XIV) in the same manner as described above and then condensing the resulting compound with the compound of formula $R^{11}OH$. The isopropylidene is then removed therefrom in the same manner as described above to prepare the compound of formula (IIIa').

The compound of formula (IIIa') wherein $R^{11}$ and $R^{21}$ are the same can also be obtained by removing $Y^1$ from the compound of formula (XIII) and condensing the resulting compound with a fatty acid, followed by removing the isopropylidene.

Reaction Route (b):

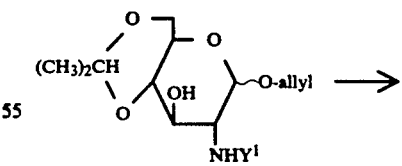

(XVI)

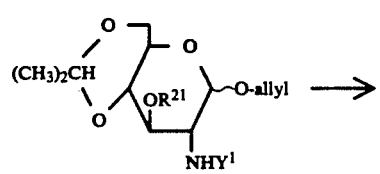

(XVII)

-continued
Reaction Route (b):

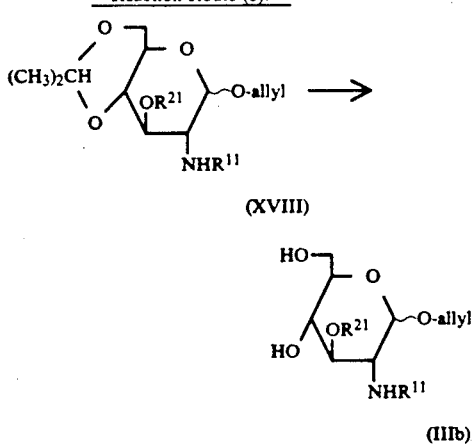

(XVIII)

(IIIb)

wherein $Y^1$, $R^{21}$, and $R^{11}$ are as defined above.

The compound of formula (XVI) is condensed with the compound of formula $R^{21}OH$ to prepare the compound of formula (XVII). After $Y^1$ is removed in the same manner as described above, the compound is condensed with the compound of formula $R^{11}OH$ to obtain the compound of formula (XVIII). The isopropylidene is then removed from the compound of formula (XVIII) in the same manner as described above to obtain the compound of formula (IIIb).

The compounds according to the present invention exhibit antitumor activity equal to or even higher than that of Compound A and have remarkably lower toxicity as compared with Compound A. Therefore, the compounds of the invention are superior as antitumor agents.

The present invention is now illustrated in greater detail with reference to Reference Examples, Examples, and Test Examples, but it should be understood that the present invention is not to be construed as limited thereto. In these examples, all the percents are by weight unless otherwise indicated.

REFERENCE EXAMPLE 1

1) Preparation of 2-acetoxyethyl 3,4,6-tri-O-acetyl-2-deoxy-2-(2,2,2-trichloroethoxycarbonylamino)-α-D-glucopyranoside To 5.00 g of 2-deoxy-2-(2,2,2-trichloroethoxycarbonylamino)-D-glucose was added 5.0 ml of ethylene glycol and 0.5 ml of dioxane containing hydrogen chloride gas, and the mixture was stirred for 4 hours under heating to 90° C. After cooling with ice-water, 75 ml of pyridine and then 30.6 g of acetic anhydride were added to the reaction mixture, followed by stirring. After 20 minutes' stirring, the reaction mixture was warmed to room temperature, and the stirring was continued for an additional 16 hours. The reaction mixture was poured into 350 ml of ice-water and stirred. The precipitated solid was collected by filtration and washed with water. The resulting solid was dissolved in chloroform, washed successively with 1N hydrochloric acid and a saturated sodium chloride aqueous solution, and dried over anhydrous sodium sulfate. The solvent was removed by distillation under reduced pressure, and the residue was recrystallized from ethanol to obtain 4.96 g of the entitled compound as a colorless prism.

Melting Point: 138°–140° C.

$[\alpha]_D^{25}: +74.0°$ (c=1.2, chloroform)

2) Preparation of 2-acetoxyethyl 3,4,6-tri-O-acetyl-2-deoxy-2-tetradecanoylamino-α-D-glucopyranoside In 60 ml of acetic acid was dissolved 4.96 g of the compound obtained in 1) above, and 7 g of zinc powder was added thereto in small portions at room temperature while stirring. The stirring was continued for 1 hour, and any insoluble matter was removed by filtration. The solvent was removed from the filtrate by distillation under reduced pressure, toluene was added to the residue, and the solvent was removed by distillation under reduced pressure. The residue was dissolved in dioxane, and dioxane containing hydrogen chloride gas was added to the solution. The solvent was removed by distillation under reduced pressure, and the residue was dried.

The resulting oily product was dissolved in 70 ml of anhydrous methylene chloride, and 2.88 ml of N-methylmorpholine and 3.24 g of tetradecanoyl chloride were added to the solution under ice-cooling, followed by stirring for 1 hour. To the reaction mixture was added 10 ml of methanol. After stirring at room temperature for 10 minutes, the reaction mixture was diluted with chloroform, washed successively with 1N hydrochloric acid and a saturated sodium chloride aqueous solution, and dried over anhydrous sodium sulfate. The solvent was distilled off under reduced pressure, and the residue was purified by silica gel column chromatography using, as an eluent, a mixture of benzene and ethyl acetate at a ratio of 9/1 (v/v) and then 1/1 (v/v) to obtain 4.77 g of the entitled compound as a colorless oily product.

3) Preparation of 2-hydroxyethyl-2-deoxy-2-tetradecanoylamino-α-D-glucopyranoside In 80 ml of absolute methanol was dissolved 4.77 g of the compound obtained in 2) above, and a methanol solution containing 9 mmol of sodium methylate was added to the solution while ice-cooling, followed by stirring at room temperature for 30 minutes. Tetrahydrofuran was added thereto to dissolve the precipitate, the solution was neutralized with a strongly acidic ion exchange resin, Dowex-50 (H+type), and the resin was filtered off. The solvent was removed from the filtrate by distillation under reduced pressure. The residue was washed with diethyl ether, followed by filtration, to give 3.02 g of the entitled compound as a white solid. Recrystallization from ethanol-water gave a purified product having a melting point of 158 to 160° C.

$[\alpha]_D^{25}: +8.21°$ [c=0.8, tetrahydrofuran:water=4:1 (v/v)]

4) Preparation of 2-hydroxyethyl 2-deoxy-4,6-O-isopropylidene-2-tetradecanoylamino-α-D-glucopyranoside In 20 ml of dimethylformamide was dissolved 0.87 g of the compound obtained in 3) above, and 0.62 g of 2,2-dimethoxypropane and 38 mg of p-toluenesulfonic acid monohydrate were added to the solution at room temperature, followed by stirring for 1.5 hours. After neutralizing with a 5% aqueous solution of sodium hydrogencarbonate, the solvent was removed by distillation under reduced pressure. The residue was dissolved in ethyl acetate, washed successively with water and a saturated sodium chloride aqueous solution, and dried over anhydrous sodium sulfate. The solvent was removed by distillation under reduced pressure, and the residue was purified by silica gel column chromatographay using, as an eluent, a 19/1 (v/v) mixture of chloroform and acetone and then a 19/1 (v/v) mixture of chloroform and methanol to obtain 0.78 g of the entitled compound as a colorless and viscous oily product.

5) Preparation of 2-(diphenylphosphonoxy)ethyl-2-deoxy-4,6-O-isopropylidene-2-tetradecanoylamino-α-glucopyranoside In 15 ml of anhydrous methylene chloride was dissolved 0.77 g of the compound obtained in 4) above, and to the solution were added 0.48 g of diphenyl phosphorochloridate, 0.19 ml of pyridine, and 0.30 g of dimethylaminopyridine under ice-cooling. After stirring for 1 hour, the temperature of the mixture was returned to room temperature, and the stirring was continued for an additional one hour. To the reaction mixture, 0.17 g of diphenyl phosphorochloridate was added thereto, followed by stirring for 30 minutes. To the reaction mixture was added 3 ml of methanol. After stirring for a while, the solvent was removed by distillation under reduced pressure. The residue was purified by silica gel column chromatography using a 19/1 (v/v) mixture of chloroform and acetone as an eluent to obtain 0.81 g of the entitled compound as a colorless viscous oil.

6) Preparation of 2-(diphenylphosphonoxy)ethyl 2-deoxy-3-O-(N-dodecanoylglycyl)-2-tetradecanoylamino-α-D-glucopyranoside In 5 ml of anhydrous methylene chloride was dissolved 0.51 g of the compound obtained in 5) above, and 0.22 g of N-dodecanoylglycine, 44 mg of dimethylaminopyrid, and 0.18 g of dicyclohexylcarbadiimide were added to the solution under ice-cooling. The mixture was stirred for 30 minutes under ice-cooling and then at room temperature for 2 hours. The insoluble matter was removed by filtration, and the filtrate was washed successively with 1N hydrochloric acid, water, and a saturated sodium chloride aqueous solution, and dried over anhydrous sodium sulfate. The solvent was removed by distillation under reduced pressure, and to the residue was added 20 ml of a 90% acetic acid aqueous solution, followed by stirring for 30 minutes while heating at 90° C. The solvent was distilled off, and toluene was added to the residue, followed by distillation to remove the solvent. Addition of toluene and subsequent distillation were repeated once more. The residue was purified by silica gel column chromatography using, as an eluent, a 19:1 (v/v) mixture of chloroform and acetone and then a 19:1 (v/v) mixture of chloroform and methanol to obtain 0.51 g of the entitled compound as a colorless oily product.

$[\alpha]_D^{25}: +46.2°$ (c=1.1, chloroform)

NMR (CDCl$_3$), δ(ppm): 0.88 (6H, t), 1.26 (s), 2.07 (2H, t), 2.27 (2H, t), 4.84 (1H, d), 5.18 (1H, m), 7.2–7.4 (10H, m)

REFERENCE EXAMPLE 2

1) Preparation of 2-hydroxyethyl 2-deoxy-2-(2,2,2-trichloroethoxycarbonylamino)-α-D-glucopyranoside In 6 ml of 28% aqueous ammonia and 120 ml of methanol was suspended 5.05 g of the compound prepared in Reference Example 1-1), and the suspension was stirred at room temperature for 8 hours. The reaction mixture was concentrated under reduced pressure to obtain 3.50 g of the entitled compound as a caramel-like substance.

NMR (CDCl$_3$—CD$_3$OD, ca. 1:1), δ(ppm): 4.78 (2H, s), 4.90 (1H, d)

2) Preparation of 2-hydroxyethyl-2-deoxy-4,6-O-isopropylidene-2-(2,2,2-trichloroethoxycarbonylamino)-α-D-glucopyranoside The compound (3.58 g) obtained in 1) above was treated in the same manner as in Reference Example 1-4). To the resulting fraction was added n-hexane, and the precipitate formed was collected by filtration to yield 2.78 g of the entitled compound as a white powder.

Melting Point: 190°–192° C.

3) Preparation of 2-(diphenylphosphonoxy)ethyl 2-deoxy-4,6-O-isopropylidene-2-(2,2,2-trichloroethoxycarbonylamino)-α-D-glucopyranoside The compound (1.12 g) obtained in 2) above was treated in the same manner as in Reference Example 1-5), and to the resulting fraction was added diethyl ether and n-hexane. The precipitate formed was collected by filtration to obtain 1.23 g of the entitled compound.

Melting Point: 121°–124° C.

$[\alpha]_D^{25}: +46.4°$ (c=1.0, chloroform)

4) Preparation of 2-(diphenylphosphonoxy)ethyl 2-deoxy-4,6-O-isopropylidene-3-O-tetradecanoyl-2-(2,2,2-trichloroethoxycarbonylamino)-α-D-glucopyranoside In 10 ml of anhydrous methylene chloride was dissolved 0.50 g of the compound obtained in 3) above, and 0.30 ml of pyridine, 0.22 g of tetradecanoyl chloride, and 20 ml of dimethylaminopyridine were added to the solution, followed by stirring for 2 hours. To the reaction mixture was added 2 ml of methanol. After stirring at room temperature for a while, the reaction mixture was concentrated under reduced pressure. The residue was purified by silica gel column chromatography using 2% acetone-containing chloroform and then 5% acetone-containing chloroform as eluents to give 0.49 g of the entitled compound as a colorless oily substance.

$[\alpha]_D^{25}: +36.1°$ (c=1.0, chloroform)

5) Preparation of 2-(diphenylphosphonoxy)ethyl 2-deoxy-2-(N-dodecanoylglycylamino)-4,6-O-isopropylidene-3-O-tetradecanoyl-α-D-glucopyranoside In 12 ml of acetic acid was dissolved 0.47 g of the compound obtained in 4) above, and 0.5 g of zinc powder was suspended therein, followed by stirring at room temperature for about 1.5 hours. Any insoluble matter was removed by filtration, the filtrate was washed with chloroform, and the solvent was removed by distillation under reduced pressure. The residue was dissolved in chloroform, washed successively with a 5% sodium hydrogen carbonate aqueous solution, and a saturated sodium chloride aqueous solution, and dried over anhydrous sodium sulfate. The solvent was distilled off, and the residual oily substance was dissolved in 8 ml of anhydrous methylene chloride. To the solution was added 0.21 g of N-dodecanoylglycine. To the mixture were added 0.17 g of dicyclohexylcarbodiimide and 32 mg of dimethylaminopyridine under ice-cooling. After 20 minutes, the temperature of the mixture was returned to room temperature, and the mixture was allowed to react for 15 hours while stirring. Any insoluble matter was removed by filtration, and the solvent was removed from the filtrate by distillation under reduced pressure. The residue was purified by silica gel column chromatography using chloroform containing 2 to 10% acetone as an eluent. The desired fraction was treated with n-hexane to obtain 0.48 g of the entitled compound as a white powder.

Melting Point: 79°-80° C.

$[\alpha]_D^{25}$: +28.1° (c=1.1, chloroform)

6) Preparation of 2-(diphenylphosphonoxy)ethyl 2-deoxy-2-(N-dodecanoylglycylamino)-3-O-tetradecanoyl-α-D-glucopyranoside In 20 ml of a 90% aqueous acetic acid solution was dissolved 0.45 g of the compound prepared in 5) above, and the solution was stirred for 30 minutes while heating at 90° C. The solvent was removed by distillation under reduced pressure, and toluene was added to the residue, followed by distillation under reduced pressure. Addition of toluene and the subsequent distillation were repeated, and the finally obtained residue was purified by silica gel column chromatography using, as an eluent, chloroform containing 5 to 10% acetone and then a 19:1 (v/v) mixture of chloroform and methanol to obtain 0.39 g of the entitled compound as a white waxy solid.

$[\alpha]_D^{25}$: +36.1° (c=1.1, chloroform)

NMR (CDCl$_3$), δ(ppm): 0.90 (6H, t), 1.28 (s), 2.13 (2H, m), 2.36 (2H, t), 4.90 (1H, d), 7.2–7.5 (10H, m)

REFERENCE EXAMPLE 3

1) Preparation of 2-(diphenylphosphonoxy)ethyl 2-deoxy-3-O-(N-dodecanoylglycyl)-4,6-O-isopropylidene-2-(2,2,2-trichloroethoxycarbonylamino)-α-D-glucopyranoside In 20 ml of anhydrous methylene chloride was dissolved 1.89 g of the compound obtained in Reference example 2-3), and 0.83 g of N-dodecanoylglycine, 0.17 g of dimethylaminopyridine, and 0.67 g of dicyclohexylcarbodiimide were added thereto while ice-cooling. After 30 minutes, the mixture was allowed to warm to room temperature and stirred for 1 hour at that temperature. Any insoluble matter was removed by filtration, and the filtrate was concentrated under reduced pressure. The residue was purified by silica gel column chromatography using a 10:1 (v/v) mixture of chloroform and acetone as an eluent to obtain 2.80 g of the entitled compound as a colorless oily substance.

$[\alpha]_D^{25}$: +32.2° (c=0.8, chloroform)

2) Preparation of 2-(diphenylphosphonoxy)ethyl-2-deoxy-3-O-(N-dodecanoylglycyl)-2-[6-(octanoylamino)hexanoylamino]-α-D-glucopyranoside In 10 ml of acetic acid was dissolved 0.71 g of the compound obtained in 1) above, and 0.5 g of a zinc powder was added thereto at room temperature while stirring. After stirring for 2 hours, the insoluble matter was removed by filtration, the filtrate was washed with chloroform, and the solvent was distilled off. The residue was dissolved in chloroform, washed successively with a 5% sodium hydrogencarbonate aqueous solution and a saturated aqueous sodium chloride solution, and dried over anhydrous magnesium sulfate. The solvent was removed by distillation under reduced pressure to obtain an oily product.

Separately, 0.26 g of 6-(octanoylamino)caproic acid was dissolved in 7 ml of anhydrous tetrahydrofuran, and 0.16 g of 1-hydroxybenzotriazole and 0.21 g of dicyclohexylcarbodiimide were added to the solution under ice-cooling. The liquid temperature was gradually returned to room temperature, and the mixture was stirred for 3 hours. The precipitated insoluble matter was removed by filtration. The filtrate was combined with the above-prepared oily product under ice-cooling, followed by warming up to room temperature, at which the mixture was stirred for 4 hours. The solvent was distilled off, and to the residue was added 20 ml of a 90% aqueous acetic acid solution. The mixture was stirred for 20 minutes under heating at 90° C. The solvent was distilled off, and the residue was purified by silica gel column chromatography using successive eluents of a 10:1 (v/v) mixture of chloroform and acetone, a 20:1 (v/v) mixture of chloroform and methanol, and a 10:1 (v/v) mixture of chloroform and methanol to thereby obtain 0.56 g of the entitled compound as a colorless waxy substance.

$[\alpha]_D^{25}$: +31.2° (c=1.1, chloroform)

NMR (CDCl$_3$), δ(ppm): 0.88 (6H, t), 2.0–2.4 (6H, m), 4.85 (1H, d), 7.2–7.4 (10H, m)

REFERENCE EXAMPLE 4

Preparation of 2-(diphenylphosohonoxy)ethyl 2-deoxy-3-O-(N-dodecanoyl-N-methylglycyl)-2-[(N-dodecanoyl-N-methylglycyl)amino]-α-D-glucopyranoside In 10 ml of acetic acid was dissolved 1.00 g of the compound obtained in Reference Example 2-3), and 0.5 g of zinc powder was added to thereto at room temperature while stirring. The stirring was continued for an additional 2.5 hours, and the insoluble matter was removed by filtration. The filtrate was washed with chloroform, and the solvent was removed by distillation under reduced pressure. The residue was dissolved in chloroform, washed successively with a 5% aqueous solution of sodium hydrogencarbonate and a saturated aqueous solution of sodium chloride, and dried over anhydrous sodium sulfate. The solvent was removed by distillation under reduced pressure, and the residual oily substance and 1.21 g of N-dodecanoyl-N-methylglycine were dissolved in 10 ml of anhydrous methylene chloride. To the solution were added 90 mg of dimthylaminopyridine and 0.92 g of dicyclohexylcarbodiimide under ice-cooling. After warming to room temperature, the mixture was stirred for 3 hours. The precipitated insoluble matter was removed by filtration, and the filtrate was concentrated under reduced pressure. The residual oily substance was purified by silica gel column chromatography successively using a 9:1 (v/v) mixture of chloroform and acetone and a 19:1 (v/v) mixture of chloroform and methanol as an eluent to obtain an oily substance. The resulting oily substance was dissolved in 40 ml of a 90% aqueous acetic acid solution, followed by stirring for 30 minutes under heating at 90° C. The solvent was removed by distillation under reduced pressure, and the residue was purified by silica gel column chromatography using, as an eluent, a mixture of chloroform and methanol at a ratio of 50:1 (v/v) and then 20:1 (v/v) to obtain 0.87 g of the entitled compound as an oily product.

$[\alpha]_D^{25}$: +34.9° (c=1.0, chloroform)

NMR (CDCl$_3$), δ(ppm): 0.89 (6H, t), 1.28 (s), 2.36 (4H, m), 2.84 and 3.00 (total 3H, each s), 3.13 and 3.15

(total 3H, each s), 4.45 (2H, m), 4.87 (1H, d), 7.2–7.4 (10H, m)

REFERENCE EXAMPLE 5

Preparation of 2-(diphenylphosphonoxy)ethyl 2-deoxy-3-O-tetradecanoyl-2-(2,2,2-trichloroethoxycarbonylamino)-α-D-glucopyranoside In 15 ml of anhydrous methylene chloride were dissolved 0.50 g of the compound obtained in Reference Example 2-3) and 0.22 g of tetradecanoic acid, and 0.12 g of dimethylaminopyridine and 0.20 g of dicyclohexylcarbodiimide were added to the solution under ice-cooling. The mixture was warmed to room temperature and stirred for 2 hours. The precipitated insoluble matter was removed by filtration, and the filtrate was concentrated under reduced pressure. The residual oily substance was subjected to silica gel column chromatography using a 10:1 (v/v) mixture of chloroform and acetone as an eluent to obtain an oily substance. The resulting oily substance was dissolved in 10 ml of a 90% aqueous acetic acid solution, followed by stirring for 25 hours while heating at 90° C. The solvent was removed by distillation under reduced pressure, and the residue was purified by silica gel column chromatography using, as eluent, a 10:1 (v/v) mixture of chloroform and acetone and then a 10:1 (v/v) mixture of chloroform and methanol to obtain 0.61 g of an oily product.

$[\alpha]_D^{25}: +43.0°$ (c=1.2, chloroform)

2) Preparation of 2-(diphenylphosphonoxy)ethyl 2-deoxy-2-[(N-dodecanoyl-D-isoglutaminyl)amino]-3-O-tetradecanoyl-α-D-glucopyranoside The compound (0.47 g) obtained in 1) above was treated with a zinc powder in an acetic acid solution and then reacted with N-dodecanoyl-D-isoglutamine in the same manner as in Reference Example 3-2) to obtain 0.36 g of the entitled compound as a white waxy substance.

$[\alpha]_D^{25}: +38.7°$ (c=0.1, chloroform)
NMR (CDCl$_3$), δ(ppm): 0.88 (6H, t), 1.26 (s), 2.1–2.5 (6H, m), 4.96 (1H, d), 5.18 (1H, d), 7.2–7 5 (10H, m)

REFERENCE EXAMPLE 6

1) Preparation of 1,3-(diethoxycarbonyl)isopropyl 2-deoxy-3,4,6-tri-O-acetyl-2-(2,2,2-trichloroethoxycarbonyl-amino)-α-D-glucopyranoside To 8.00 g of 1,3,4,6-tetra-O-acetyl-2-deoxy-2-(2,2,2-trichloroethoxycarbonylamino)-D-glucopyranose was added a cooled acetic acid solution containing 25% hydrogen bromide at room temperature, followed by stirring for 1 hour. The reaction mixture was diluted with chloroform, washed successively with a 5% sodium hydrogencarbonate aqueous solution and a saturated sodium chloride aqueous solution, and dried over anhydrous magnesium sulfate. The solvent was removed by distillation under reduced pressure, and the residue was dissolved in 72 ml of anhydrous methylene chloride. To the solution were added 8 g of anhydrous calcium sulfate, a suspension of 4.12 g of silver perchlorate in 40 ml of anhydrous benzene, and 6.24 g of diethyl-3-hydroxyglutarate under ice-cooling. The mixture was allowed to react at room temperature for 3 hours, followed by neutralizing with a 5% aqueous solution of sodium hydrogencarbonate. The insoluble matter was removed by filtration, and the filtrate was washed with water and dried over anhydrous magnesium sulfate. The solvent was distilled off, and the residue was purified by silica gel column chromatography using 30:1 (v/v) mixture of chloroform and acetone as an eluent to obtain 7.36 g of the entitled compound as an oily substance.

$[\alpha]_D^{25}: +42.8°$ (c=0.7, chloroform)

2) Preparation of 1,3-(diethoxycarbonyl)isopropyl 2-deoxy-2-tetradecanoylamino-3,4,6-tri-O-acetyl-α-D-glucopyranoside The compound (4.00 g) obtained in 1) above was treated with zinc powder in an acetic acid solution and then reacted with tetradecanoic acid in the same manner as in Reference Example 3-2) to obtain 3.78 g of the entitled compound as an oily substance.

$[\alpha]_D^{25}: +46.9°$ (c=0.16, chloroform)

3) Preparation of 1,3-(dibenzyloxycarbonyl)isopropyl 2-deoxy-2-tetradecanoylamino-α-D-glucopyranoside In 30 ml of dioxane was dissolved 1.80 g of the compound obtained in 2) above, and 10 ml of water was added thereto. After cooling to 5° C., 15 ml of a 1N potassium hydroxide aqueous solution was added to the solution. After stirring for 6 hours, 1N hydrochloric acid was added thereto to adjust to a pH Of 7.5. The reaction mixture was concentrated to dryness under reduced pressure. The residue was suspended in 100 ml of dimethylformamide, and 1 ml of benzyl bromide was added thereto. After stirring at 40° C. for 3 hours, most of the dimethylformamide was removed by distillation under reduced pressure. The residue was extracted with benzene, and the benzene layer was washed successively with a 5% citric acid aqueous solution, a saturated sodium chloride aqueous solution, a 5% sodium hydrogencarbonate aqueous solution, and a saturated sodium chloride aqueous solution, and dried over anhydrous magnesium sulfate. The solvent was removed by distillation under reduced pressure, and the residue was purified by silica gel column chromatography using, as an eluent, a mixture of chloroform, methanol, and acetone at a volume ratio of 50:1:5 and then 50:1:15 to obtain 0.65 g of the entitled compound as a white waxy solid.

$[\alpha]_D^{25}: +13.2°$ (c=0.51, chloroform)

4) Preparation of 1,3-(dibenzyloxycarbonyl)isopropyl 2-deoxy-4,6-O-isopropylidene-2-tetradecanoylamino-α-D-glucopyranoside In 10 ml of acetone was dissolved 0.64 g of the compound obtained in 3) above and the same was treated in the same manner as in Reference Example 1-4) to obtain 0.54 g of the entitled compound as an oily substance.

$[\alpha]_D^{25}: +3.3°$ (c=0.7, chloroform)

5) Preparation of 1,3-(dibenzyloxycarbonyl)isopropyl 2-deoxy-3-O-tetradecanoyl-2-tetradecanoylamino-α-D-glucopyranoside In the same manner as in Reference Example 1-6), 0.48 g of the compound obtained in 4) above was reacted with tetradecanoic acid, and the reaction product was heated in a 90% acetic acid aqueous solution to obtain 0.53 g of the entitled compound as a white waxy solid.

$[\alpha]_D^{25}: +32.8°$ (c=0.9, chloroform) NMR (CDCl$_3$), δ(ppm): 0.88 (6H, t), 1.26 (s), 4.94 (1H), 5.20 (4H, s), 7.40 (10H, s)

REFERENCE EXAMPLE 7

Preparation of 1,3-(dibenzyloxycarbonyl)isopropyl 2-deoxy-3-O-(N-dodecanoylglycyl)-2-tetradecanoylamino-α-D-glucopyranoside In the same manner as in Reference Example 1-6), 0.60 g of the compound obtained in Reference Example 6-4) was reacted with N-dodecanoylglycine, and the reaction product was treated with a 90% acetic acid aqueous solution to obtain 0.63 g of the entitled compound as a waxy solid.

$[\alpha]_D^{25}: +36.9°$ (c=1.3, chloroform) NMR (CDCl$_3$), δ(ppm): 0.89 (6H, t), 1.26 (s), 2.1–2.3 (4H, m), 2.5–2.9 (4H, m), 4.50 (1H, m), 4.97 (1H, d), 5.07 (1H, m), 5.18 (4H), 7.40 (10H, s)

REFERENCE EXAMPLE 8

1) Preparation of 2-acetoxyethyl 3,4,6-tri-O-acetyl-2-deoxy-2-[6-(octanoylamino)hexanoylamino]-α-D-glucopyranoside In the same manner as in Reference Example 2-5), 3.00 g of the compound obtained in Reference Example 1-1) was treated with zinc powder in an acetic acid solution, and the reaction product was reacted with 6-(octanoylamino)caproic acid to obtain 2.84 g of the entitled compound as a waxy solid.

$[\alpha]_D^{25}: +55.4°$ (c=1.1, chloroform)

2) Preparation of 2-hydroxyethyl 2-deoxy-2-[6-(octanoylamino)hexanoylamino]-α-D-glucopyranoside In the same manner as in Reference Example 1-3), 2.82 g of the compound obtained in 1) above was reacted to yield 1.66 g of the entitled compound as a white powder.

Melting Point: 156°–157° C.
$[\alpha]_D^{25}: +78.8°$ (c=0.9, ethanol)

3) Preparation of 2-hydroxyethyl 2-deoxy-4,6-O-isopropylidene-2-[6-(octanoylamino)hexanoylamino]-α-D-glucopyranoside In the same manner as in Reference Example 1-4), 1.60 g of the compound prepared in 2) above was reacted to yield 1.48 g of the entitled compound as an oily substance.

$[\alpha]_D^{25}: +35.2°$ (c=1.0, chloroform)

4) Preparation of 2-(diphenylphosphonoxy)ethyl 2-deoxy-4,6-O-isopropylidene-2-[6-(octanoylamino)hexanoylamino]-α-D-glucopyranoside In the same manner as in Reference Example 1-5), 1.26 g of the compound obtained in 3) above was reacted to obtain 1.35 g of the entitled compound as an oily substance.

$[\alpha]_D^{25}: +26.7°$ (c=1.2, chloroform)

5) Preparation of 2-(diphenylphosphonoxy)ethyl 2-deoxy-3-O-dodecanoyl-2-[6-(octanoylamino)hexanoylamino]-α-D-glucopyranoside In the same manner as in Reference Example 1-6), 0.65 g of the compound obtained in 4) above was reacted with dodecanoic acid, and the reaction product was heated in a 90% acetic acid aqueous solution to obtain 0.73 g of the entitled compound as an oily substance.

$[\alpha]_D^{25}: +37.3°$ (c=1.1, chloroform)

NMR (CDCl$_3$), δ(ppm): 0.89 (6H, m), 2.10 (4H, m), 2.33 (2H, m), 3.20 (2H, m), 4.30 (1H, m), 4.46 (2H, m), 4.85 (1H, d), 5.10 (1H, m)

REFERENCE EXAMPLE 9

1) Preparation of 2-acetoxyethyl 3,4,6-tri-O-acetyl-2-[(R)-3-benzyloxytetradecanoylamino]-2-deoxy-α-D-glucopyranoside In the same manner as in Reference Example 2-5), 3.00 g of the compound obtained in Reference Example 1-1) was treated with zinc powder in an acetic acid solution, and the reaction product was reacted with 1.95 g of (R)-3-benzyloxytetradecanoic acid to yield 3.70 g of the entitled compound as an oily substance.

NMR (CDCl$_3$), δ(ppm): 0.87 (3H, t, J=6Hz), 2.00 (3H, s), 2.02 (3H, s), 2.04 (3H, s), 2.08 (3H, s), 2.18 (2H, m), 4.54 (2H, ABq, J=12Hz), 4.76 (1H, d, J=4Hz), 7.36 (5H, s)

2) Preparation of 2-hydroxyethyl 2-[(R)-3-benzyloxytetradecanoylamino]-2-deoxy-α-D-glucopyranoside In the same manner as in Reference Example 1-3), 3.68 g of the compound prepared in 1) above was reacted to obtain 2.49 g of the entitled compound as a pale brown powder. Recrystallized from water-ethanol.

Melting Point: 125°–127° C.
$[\alpha]_D^{25}: +73.3°$ (c=0.9, methanol)

3) Preparation of 2-hydroxyethyl 2-[(R)-3-benzyloxytetradecanoylamino]-2-deoxy-4,6-O-isopropylidene-α-D-glucopyranoside In the same manner as in Reference Example 1-4), 0.98 g of the entitled compound was obtained as a colorless oily substance from 1.20 g of the compound prepared in 2) above.

$[\alpha]_D^{25}: +31.4°$ (c=0.9, chloroform)

4) Preparation of 2-(diphenylphosphonoxy)ethyl 2-[(R)-3-benzyloxytetradecanoylamino]-2-deoxy-4,6-O-isopropylidene-α-D-glucopyranoside In the same manner as in Reference Example 1-5), 0.98 g of the entitled compound was obtained as a colorless oily substance from 0.83 g of the compound prepared in 3) above.

NMR (CDCl$_3$), δ(ppm): 0.88 (3H, t, J=7Hz), 1.46 (3H, s), 1.53 (3H, s), 2.47 (2H, d, J=6Hz), 4.2 (3H, m), 4.53 (2H, ABq, J=12Hz), 4.64 (1H, d, J=4Hz), 7.2–7.4 (15H, m)

5) Preparation of 2-(diphenylphosphonoxy)ethyl 3-O-[(R)-3-benzyloxytetradecanoyl]-2-[(R)-3-benzyloxytetradecanoylamino]-2-deoxy-α-D-glucopyranoside In the same manner as in Reference Example 1-6), 0.96 g of the compound obtained in 4) above was reacted with 0.59 g of (R)-3-benzyloxytetradecanoic acid, and the reaction product was heated with a 90% acetic acid solution to obtain 1.23 g of the entitled compound as a colorless oily substance.

$[\alpha]_D^{25}: +31.4°$ (c=1.2, chloroform)

NMR (CDCl$_3$), δ(ppm): 0.88 (6H, t, J=7Hz, 2.34 (2H, d, J=6Hz), 2.6 (2H, m), 4.51 (2H, ABq, J=12Hz), 4.56 (2H, s), 4.71 (1H, d, J=4Hz, 5.13 (1H, m), 7.2–7.4 (20H, m)

REFERENCE EXAMPLE 10

Preparation of 2-(diphenylphosphonoxy)ethyl 3-O-[(R)-3-benzyloxytetradecanoyl]-2-deoxy-2-tetradecanoylamino-α-D-glucopyranoside In the same manner as in Reference Example 1-6), the compound obtained in Reference Example 1-5) was reacted with (R)-3-benzyloxytetradecanoic acid, and the reaction product was heated in a 90% acetic acid solution to obtain the entitled compound as an oily substance.

NMR (CDCl$_3$), δ(ppm): 0.89 (6H, t), 2.06 (2H, t), 2.1–2.8 (2H, m), 4.85 (1H, d), 5.14 (1H, t), 7.1–7.3 (15H, m)

REFERENCE EXAMPLE 11

Preparation of 2-(diphenylphosphonoxy)ethyl 2-[(R)-3-benzyl-oxytetradecanoylamino]-2-deoxy-3-O-tetradecanoyl-α-D-glucopyranoside In the same manner as in Reference Example 1-6), the compound prepared in Reference Example 9-4) was reacted with tetradecanoic acid, and the reaction product was heated in a 90% acetic acid aqueous solution to obtain the entitled compound as a colorless oily substance.

NMR (CDCl$_3$), δ(ppm): 0.88 (6H, t), 2.3–2.4 (4H, m), 4.52 (2H, d), 4.72 (1H, d), 5.10 (1H, m), 7.2–7.5 (15H, m)

REFERENCE EXAMPLES 12 TO 52

In the same manner as described in Reference Examples 1 to 11, the following compounds represented by formula (IIIa) were prepared.

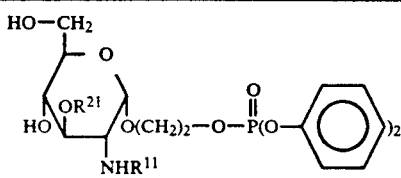

(IIIa)

| Reference Examples | R$^{21}$ | R$^{11}$ | Physical Properties |
|---|---|---|---|
| 12 | —CO(CH$_2$)$_5$NHCO(CH$_2$)$_6$CH$_3$ | —CO(CH$_2$)$_{12}$CH$_3$ | [α]$_D^{25}$: +30.3° (c=1.0, chloroform) NMR (CDCl$_3$), δ(ppm): 0.89(6H, t), 2.06(2H, t), 2.19(2H, t), 2.35(2H, m), 3.10(1H), 3.30(1H), 4.3–4.5(4H, m), 4.85(1H, d), 5.18(1H, m), 7.2–7.4(10H, m) |
| 13 | —COCH$_2$NHCO(CH$_2$)$_{10}$CH$_3$ | —CO(CH$_2$)$_2$NHCO(CH$_2$)$_8$CH$_3$ | [α]$_D^{25}$: +24.3° (c=0.8, chloroform) NMR (CDCl$_3$), δ(ppm): 0.88(6H, t), 1.9–2.5 (6H, m), 3.25(1H, m), 3.52(1H, m), 3.7–4.5(7H, m), 4.84(1H, d), 5.20(1H, t), 7.2–7.5(10H, m) |
| 14 | —COCH$_2$NHCO(CH$_2$)$_{10}$CH$_3$ | —CO(CH$_2$)$_3$NHCO(CH$_2$)$_8$CH$_3$ | [α]$_D^{25}$: +32.5° (c=0.7 chloroform) NMR (CDCl$_3$), δ(ppm): 0.88(6H, t), 2.0–2.4 (6H, m), 4.83(1H, d), 5.22(1H, t), 7.1–7.5(10H, m) |
| 15 | —COCH$_2$NHCO(CH$_2$)$_{10}$CH$_3$ | CH$_3$<br>\|<br>—COCH$_2$NCO(CH$_2$)$_{10}$CH$_3$ | [α]$_D^{25}$: +33.8° (c=1.0, chloroform) NMR (CDCl$_3$), δ(ppm): 0.88(6H, t), 1.28(s), 2.2–2.4(4H, m), 2.98(3H, s), 4.85(1H, d), 5.22(1H, t), 7.2–7.5(10H, m) |
| 16 | —COCH$_2$NHCO(CH$_2$)$_{10}$CH$_3$ | (CH$_2$)$_{11}$CH$_3$<br>\|<br>—COCH$_2$NCO(CH$_2$)$_{10}$CH$_3$ | [α]$_D^{25}$: +31.4° (c=1.0, chloroform) NMR (CDCl$_3$), δ(ppm): 0.88(9H, t), 1.26(s), 2.2–2.4(4H, m), 3.1–3.4(2H, br), 4.84(1H, d), 5.21(1H, t), 7.2–7.5(10H, m) |
| 17 | —COCH$_2$NHCO(CH$_2$)$_{10}$CH$_3$ | CH$_3$<br>\|<br>—COCHNHCO(CH$_2$)$_{10}$CH$_3$ | [α]$_D^{25}$: +29.6° (c=0.2, chloroform) NMR (CDCl$_3$), δ(ppm): 0.88(6H, t), 1.26(s), 1.9–2.5(8H, m), 3.51(2H, m), 4.80(1H, m), 5.20(1H, m), 7.2–7.5(10H, m) |
| 18 | —COCH$_2$NHCO(CH$_2$)$_{10}$CH$_3$ | —COCH$_2$OCO(CH$_2$)$_{10}$CH$_3$ | [α]$_D^{25}$: +35.5° (c=1.3, chloroform) NMR (CDCl$_3$), δ(ppm): 0.90(6H, t), 1.28(s), 2.28(2H, t), 2.40(2H, t), 4.45(s), 4.85 (1H, d), 5.22(1H, m), 7.2–7.5(10H, m) |
| 19 | —COCH$_2$NHCO(CH$_2$)$_{10}$CH$_3$ | CH$_3$<br>\|<br>—CO(CH$_2$)$_5$NCO(CH$_2$)$_6$CH$_3$ | [α]$_D^{25}$: +14.3° (c=0.5, chloroform) NMR (CDCl$_3$), δ(ppm): 0.88(6H, t), 1.26(s), 2.10(2H, m), 2.30(4H, m), 2.90, 2.96 (total 3H, each s), 3.30(2H, m), 4.84(1H, d), 5.20(1H, m), 7.2–7.5(10H, m) |
| 20 | —COCH$_2$NHCO(CH$_2$)$_{10}$CH$_3$ | —CO(CH$_2$)$_5$NHCO(CH$_2$)$_8$CH$_3$ | [α]$_D^{25}$: +29.9° (c=0.5, chloroform) NMR (CDCl$_3$), δ(ppm): 0.89(6H, t), 1.28(s), 2.12(4H, m), 2.28(2H, t), 3.18(2H, m), 4.84(1H, d), 7.2–7.4(10H, m) |

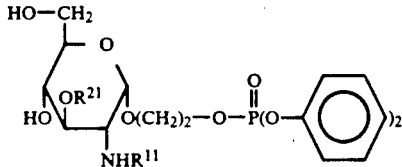

(IIIa)

| Reference Examples | $R^{21}$ | $R^{11}$ | Physical Properties |
|---|---|---|---|
| 21 | —COCH₂NHCO(CH₂)₁₀CH₃ | —COCH(CH₃)NHCO(CH₂)₁₀CH₃ | $[\alpha]_D^{25}$: +18.6 (c=1.3, chloroform) NMR (CDCl₃), δ(ppm): 0.88(6H, t), 2.30(2H, t), 4.81(1H, d), 5.23(1H, t), 7.2–7.6 (10H, m) |
| 22 | —COCH₂NHCO(CH₂)₁₀CH₃ | —COCH(CH₃)N(CH₃)CO(CH₂)₁₀CH₃ | $[\alpha]_D^{25}$: +29.1° (c=1.0, chloroform) NMR (CDCl₃), (ppm): 0.88(6H, t), 2.2–2.5, (4H, m), 2.84, 2.93(total 3H, each s), 4.91(1H, d), 5.20(1H, m), 7.2–7.5(10H, m) |
| 23 | —COCH₂NHCO(CH₂)₁₀CH₃ | —CO(CH₂)₂CO(CH₂)₂NHCO(CH₂)₆CH₃ | $[\alpha]_D^{25}$: +25.4° (c=0.37, chloroform) NMR (CDCl₃), δ(ppm): 0.88(6H, t), 1.26(s), 3.48(2H, m), 4.06(2H, d), 4.25(1H, m), 4.44(2H, m), 4.81(1H, d), 5.20(1H, t), 7.2–7.5(10H, m) |
| 24 | —COCH₂NHCO(CH₂)₈CH₃ | —CO(CH₂)₈CH₃ | $[\alpha]_D^{25}$: +46.6° (c=1.1, chloroform) NMR (CDCl₃), δ(ppm): 0.89(6H, t), 1.28(s), 2.08(2H, m), 2.28(2H, t), 4.84(d, 1H), 5.20(1H, m), 7.2–7.4(10H, m) |
| 25 | —COCH₂NHCO(CH₂)₆CH₃ | —CO(CH₂)₈CH₃ | $[\alpha]_D^{25}$: +50.4° (c=1.0, chloroform) NMR (CDCl₃), δ(ppm): 0.89(6H, t), 1.28(s), 2.08(2H, t), 2.28(2H, t), 4.84(d, 1H), 5.20(1H, m), 7.2–7.4(10H, m) |
| 26 | —CO(CH₂)₂NHCO(CH₂)₈CH₃ | —CO(CH₂)₁₂CH₃ | $[\alpha]_D^{25}$: +33.0° (c=0.6, chloroform) NMR (CDCl₃), δ(ppm): 0.88(6H, t), 1.26(s), 2.0–2.5(6H, m), 4.84(1H, d), 5.26(1H, m), 7.2–7.5(10H, m) |
| 27 | —COCH₂NHCO(CH₂)₈CH₃ | —CO(CH₂)₁₀CH₃ | $[\alpha]_D^{25}$: +49.6° (c=0.92, chloroform) NMR (CDCl₃), δ(ppm): 0.89(6H, t), 1.28(s), 2.08(2H, t), 2.28(2H, t), 4.84(1H, d), 5.20(1H, m), 7.2–7.4(10H, m) |
| 28 | —CO(CH₂)₂CO(CH₂)₉CH₃ | —CO(CH₂)₁₂CH₃ | $[\alpha]_D^{25}$: +33.0° (c=0.4, chloroform) NMR (CDCl₃), δ(ppm): 0.88(6H, t), 1.26(s), 2.09(2H, t), 2.46(2H, t), 2.56(2H, t), 2.80(2H, m), 4.84(1H, d), 5.16(1H, m), 7.2–7.5(10H, m) |
| 29 | —COCH₂N(CH₃)—CO(CH₂)₁₀CH₃ | —CO(CH₂)₅NHCO(CH₂)₆CH₃ | $[\alpha]_D^{25}$: +29.8° (c=0.45, chloroform) NMR (CDCl₃), δ(ppm): 0.88(6H, t), 1.26(s), 2.08(4H, m), 2.38(2H, t), 3.16(3H, s), 4.84(1H, d), 5.18(1H, m), 7.2–7.5(10H, m) |
| 30 | —CO(CH₂)₁₂CH₃ | —CO(CH₂)₅NHCO(CH₂)₆CH₃ | $[\alpha]_D^{25}$: +39.4° (c=0.7, chloroform) NMR (CDCl₃), δ(ppm): 0.88(6H, t), 1.26(s), 2.0–2.5(6H, m), 4.85(1H, d), 5.09(1H, m), 7.2–7.5(10H, m) |
| 31 | —CO(CH₂)₁₂CH₃ | —CO(CH₂)₃NHCO(CH₂)₈CH₃ | $[\alpha]_D^{25}$: +41.3 (c=0.9, chloroform) NMR (CDCl₃), δ(ppm): 0.88(6H, t), 2.0–2.4 (6H, m), 4.84(1H, d), 5.09(1H, m), 7.2–7.5(10H, m) |
| 32 | —COCH₂N(CH₃)CO(CH₂)₁₀CH₃ | —CO(CH₂)₁₂CH₃ | $[\alpha]_D^{25}$: +25.43° (c=1.14, chloroform) NMR (CDCl₃), δ(ppm): 0.88(6H, t), 1.28(s), 2.08(2H, m), 2.38(2H, t), 3.14(3H, s), 4.83(1H, d), 5.19(1H, m), 7.2–7.5(10H, m) |
| 33 | —CO(CH₂)₁₂CH₃ | —CO(CH₂)₇NHCO(CH₂)₄CH₃ | $[\alpha]_D^{25}$: +37.4° (c=1.5, chloroform) NMR (CDCl₃), δ(ppm): 0.88(6H, t), 2.0–2.2, (4H, m), 2.34(2H, t), 3.2–3.3(2H, m), 4.85(1H, d), 5.1–5.2(1H, m), 7.2–7.4(10H, m) |
| 34 | —CO(CH₂)₁₂CH₃ | —COCH₂N(CH₃)CO(CH₂)₁₀CH₃ | $[\alpha]_D^{25}$: +42.7° (c=1.8, chloroform) NMR (CDCl₃), δ(ppm): 0.90(6H, t), 1.28(s), 2.36(4H, t), 2.86 and 3.02(total 3H, each s), 4.42(1H, m), 4.46(2H, m), 4.89(1H, d), 5.07(1H, m), 7.2–7.4(10H, m) |

-continued

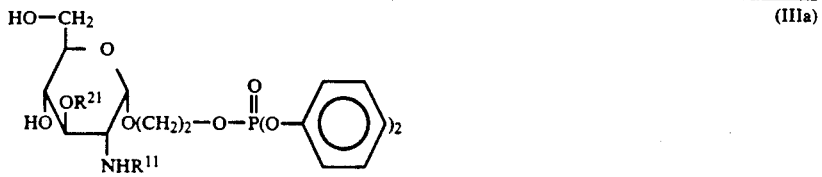

(IIIa)

| Reference Examples | R²¹ | R¹¹ | Physical Properties |
|---|---|---|---|
| 35 | —COCH(CH₃)NCO(CH₂)₁₀CH₃ with CH₃ | —CO(CH₂)₁₂CH₃ | $[\alpha]_D^{25}$: +23.7° (c=0.8, chloroform) NMR (CDCl₃), δ(ppm): 0.90(6H, t), 2.06(2H, t), 2.34(2H, t), 3.02 and 3.12(total 3H, each s), 4.18(1H, d), 5.24(1H, t), 7.2-7.5(10H, m) |
| 36 | —CO(CH₂)₂CO(CH₂)₉CH₃ | —CO(CH₂)₂CO(CH₂)₉CH₃ | $[\alpha]_D^{25}$: +24.0° (c=0.5, chloroform) NMR (CDCl₃), δ(ppm): 0.88(6H, t), 1.26(br), 2.3-2.8(12H, m), 4.2-4.5(4H, m), 4.82(1H, d), 5.18(1H, m), 6.56(1H, m), 7.2-7.5(10H, m) |
| 37 | —COCH₂NHCO(CH₂)₈CH₃ | —CO(CH₂)₁₂CH₃ | $[\alpha]_D^{25}$: +39.1° (c=1.0, chloroform) NMR (CDCl₃), δ(ppm): 0.89(6H, t), 1.28 (br), 2.08(2H, t), 2.28(2H, t), 4.84(1H, d), 5.18(1H, m), 7.2-7.5(10H, m) |
| 38 | —COCH₂NHCO(CH₂)₁₀CH₃ | —CO(CH₂)₁₀CH₃ | $[\alpha]_D^{25}$: +41.0° (c=1.8, chloroform) NMR (CDCl₃), δ(ppm): 0.89(6H, t), 1.29 (br), 2.08(2H, t), 2.28(2H, t), 4.83(1H, d), 5.18(1H, m), 7.2-7.5(10H, m) |
| 39 | —CO(CH₂)₂CO(CH₂)₉CH₃ | —COCH₂N(CH₃)CO(CH₂)₁₀CH₃ | $[\alpha]_D^{25}$: +29.4° (c=1.0, chloroform) NMR (CDCl₃), δ(ppm): 0.88(6H, t), 1.26 (br), 2.2-2.9(8H, m), 3.02 and 3.10(total 3H, each s), 4.46(2H, m), 4.88(1H, d), 5.16(1H, m), 7.2-7.5(10H, m) |
| 40 | —CO(CH₂)₂CO(CH₂)₉CH₃ | —CO(CH₂)₅NHCO(CH₂)₆CH₃ | $[\alpha]_D^{25}$: +25.0° (c=0.5, chloroform) |
| 41 | —COCH₂CO(CH₂)₁₀CH₃ | —CO(CH₂)₇NHCO(CH₂)₄CH₃ | $[\alpha]_D^{25}$: +31.7° (c=1.0, chloroform) |
| 42 | —COCH₂NHCO(CH₂)₁₀CH₃ | —COCH₂NHCO(CH₂)₁₀CH₃ | $[\alpha]_D^{25}$: +16.6° (c=0.8, chloroform) NMR (CDCl₃), δ(ppm): 0.90(6H, t), 1.28(s), 2.0-2.3(4H, m), 4.85(1H, d), 5.24(1H, t), 7.2-7.5(10H, m) |
| 43 | —CO(CH₂)₅NHCO(CH₂)₆CH₃ | —CO(CH₂)₅NHCO(CH₂)₆CH₃ | $[\alpha]_D^{25}$: +31.6° (c=1.2, chloroform) NMR (CDCl₃), δ(ppm): 0.88(6H, t), 1.28(s), 2.0-2.2(6H, m), 2.35(2H, m), 3.1-3.3 (4H, m), 4.85(1H, d), 5.17(1H, m), 7.2-7.4 (10H, m) |
| 44 | —CO(CH₂)₁₂CH₃ | —CO(CH₂)₂CH(COOCH₂C₆H₅)NHCO(CH₂)₈CH₃ | $[\alpha]_D^{25}$: +37.7° (c=0.6, chloroform) NMR (CDCl₃), δ(ppm): 0.88(6H, t), 1.26(s), 2.0-2.2(6H, m), 2.30(2H, t), 4.82(1H, d), 5.14(2H, s), 7.2-7.5(15H, m) |
| 45 | —CO(CH₂)₁₂CH₃ | —COCH₂—C₆H₁₁ (cyclohexyl) | $[\alpha]_D^{25}$: +42.1° (c=1.3, chloroform) NMR (CDCl₃), δ(ppm): 0.90(3H, t), 1.26(s), 1.3-1.8(br), 2.00(s), 2.34(2H, m), 4.84(1H, d), 7.2-7.5(10H, m) |
| 46 | —CO(CH₂)₁₂CH₃ | —COCH₂NHCOCH₂—C₆H₁₁ (cyclohexyl) | $[\alpha]_D^{25}$: +34.3° (c=1.6, chloroform) NMR (CDCl₃), δ(ppm): 0.88(3H, t), 1.26(s), 1.3-1.8(br), 2.04(m), 2.36(2H, t), 4.88(1H, d), 7.2-7.5(10H, m) |
| 47 | —COCH(CH₃)NHCO(CH₂)₁₀CH₃ | —CO(CH₂)₁₂CH₃ | $[\alpha]_D^{25}$: +20.4° (c=0.9, chloroform) NMR (CDCl₃), δ(ppm): 0.88(3H, t), 2.22(2H, t), 4.90(1H, d), 5.22(1H, m), 7.2-7.5 (10H, m) |
| 48 | —CO(CH₂)₁₂CH₃ | —CO(CH₂)₁₂CH₃ | $[\alpha]_D^{25}$: +40.8° (c=1.1, chloroform) |
| 49 | —CH(CH₂)₆CH₃ | —CO(CH₂)₆CH₃ | $[\alpha]_D^{25}$: +49.4° (c=1.2, chloroform) NMR (CDCl₃), δ(ppm): 0.86(6H, m), 2.08 (2H, t), 2.36(2H, t), 4.85(1H, d), 5.10 (1H, m), 7.2-7.5(10H, m) |
| 50 | —CO(CH₂)₈CH₃ | —CO(CH₂)₈CH₃ | $[\alpha]_D^{25}$: +46.1° (c=0.8, chloroform) NMR (CDCl₃), δ(ppm): 0.88(6H, t), 2.07 (2H, t), 2.35(2H, t), 4.85(1H, d), 5.10 (1H, m), 7.2-7.5(10H, m) |
| 51 | —CO(CH₂)₁₀CH₃ | —CO(CH₂)₁₀CH₃ | NMR (CDCl₃), δ(ppm): 0.90(6H, t), 2.07(2H, t), 2.35(2H, t), 4.85(1H, d), 5.10(1H, |

-continued

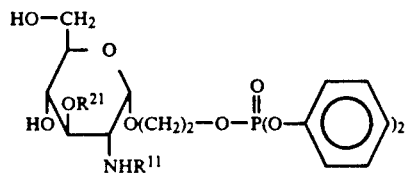
(IIIa)

| Reference Examples | $R^{21}$ | $R^{11}$ | Physical Properties |
|---|---|---|---|
| 52 | —CO(CH$_2$)$_{14}$CH$_3$ | —CO(CH$_2$)$_{14}$CH$_3$ | m), 7.2–7.5(10H, m)<br>$[\alpha]_D^{25}$: +37.2° (c=1.1, chloroform)<br>NMR (CDCl$_3$), (ppm): 0.89(6H, t), 2.06 (2H, t), 2.32(2H, t), 4.84(1H, d), 5.10 (1H, m), 7.2–7.5(10H, m) |
| 53 | —CO(CH$_2$)$_{12}$CH$_3$ | —CO(CH$_2$)$_{11}$NHCOCH$_3$ | $[\alpha]_D^{25}$: +28.5° (c=0.8, chloroform) |

In the same manner as described in Reference Examples 1 to 11, the following compounds represented by formula (IIIb) were prepared.

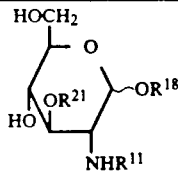

| Reference Examples | OR$^{18}$ | $R^{21}$ | $R^{11}$ | Physical Properties |
|---|---|---|---|---|
| 54 | β-O—(CH$_2$)$_2$OP(O—⌬)$_2$ with =O | —CO(CH$_2$)$_{12}$CH$_3$ | —CO(CH$_2$)$_{12}$CH$_3$ | $[\alpha]_D^{25}$: −19.5° (c = 0.9, chloroform) |
| 55 | β-OCH$_2$COOCH$_2$—⌬ | OCH$_2$—⌬ \| —COCH$_2$CH(CH$_2$)$_{10}$CH$_3$ | OCH$_2$—⌬ \| —COCH$_2$CH(CH$_2$)$_{10}$CH$_3$ | $[\alpha]_D^{25}$: −25.6° (c = 1.1, chloroform) |
| 56 | α-OCH$_2$COO—CH$_2$—⌬ | —CO(CH$_2$)$_{12}$CH$_3$ | —CO(CH$_2$)$_{12}$CH$_3$ | m.p.: 54–55° C.<br>$[\alpha]_D^{25}$: +46.9° (c = 1.1, chloroform) |

EXAMPLE 1

1) Preparation of 2-(diphenylphosphonoxy)ethyl 2-deoxy-6-O-[2-deoxy-4-O-diphenylphosphono-3-O-(N-dodecanoylglycyl)-6-O-(2,2,2-trichloroethoxycarbonyl)-2-(2,2,2-trichloroethoxycarbonylamino)-β-D-glucopyranosyl]-3-O-(N-dodecanoylglycyl)-2-[(N-dodecanoyl-N-methylglycyl)amino]-α-D-glucopyranoside In 2 ml of anhydrous methylene chloride was dissolved 370 mg of 1-O-acetyl-2-deoxy-4-O-diphenylphosphono-3-O-(N-dodecanoylglycyl)-6-O-(2,2,2-trichloroethoxycarbonyl)-2-(2,2,2-trichloroethoxycarbonylamino)-D-glucopyranose, and 6 ml of a cooled acetic acid solution containing 25% hydrogen bromide was added to the solution at room temperature, followed by stirring for 1 hour. The reaction mixture was diluted with chloroform, washed successively with ice-water, a 5% sodium hydrogencarbonate aqueous solution, and a saturated sodium chloride aqueous solution, and dried over anhydrous sodium sulfate. The solvent was removed by distillation under reduced pressure. The residue and 344 mg of 2-(diphenylphosphonoxy)ethyl 2-deoxy-3-O-(N-dodecanoylglycyl)-2-[(N-dodecanoyl-N-methylglycyl)amino]-α-D-glucopyranoside were dissolved in 5 ml of anhydrous methylene chloride. To the solution were added 0.5 g of activated calcium sulfate and 182 mg of mercury (II) cyanide, and the mixture was heated to 50° to 60° C. and stirred for 3 hours. The insoluble matter was removed by filtration through Celite, and the filtrate was washed successively with a 5% potassium iodide aqueous solution and a saturated sodium chloride aqueous solution, and dried over anhydrous sodium sulfate. The solvent was distilled off, and the residue was purified by silica gel column chromatography using, as an eluent, a 10:1 (v/v) mixture of chloroform and acetone, followed by a 50:1 (v/v) mixture of chloroform and methanol, and followed by a 20:1 (v/v) mixture of chloroform and methanol to thereby obtain 599 mg of the entitled compound as an oily substance.

$[\alpha]_D^{25}$: +20.0° (c=1.0, chloroform)

Preparation of
2-(diphenylphosphonoxy)ethyl-2-deoxy-6-O-(2-deoxy-4-O-diphenylphosphono-3-O-(N-dodecanoylglycyl)-2-[(N-dodecanoyl-N-methylglycyl)amino]-β-D-glucopyranoxy)-3-O-(N-dodecanoylglycyl)-2-[(N-dodecanoyl-N-methylglycyl)amino]-α-D-glucopyranoside In 8 ml of acetic acid was dissolved 587 mg of the compound prepared in 1) above, and 0.6 g of zinc powder was suspended in the solution, followed by stirring at room temperature for 2 hours. The insoluble matter was removed by filtration, and the filtrate was washed with chloroform. The solvent was removed by distillation under reduced pressure, and toluene was added to the residue, followed by distillation to remove the solvent. Addition of toluene and subsequent distillation were repeated three times in total, and the residue was dissolved in chloroform. The chloroform layer was washed successively with 1N hydrochloric acid, a sodium hydrogencarbonate aqueous solution, and a saturated sodium chloride aqueous solution and dried over anhydrous sodium sulfate. The solvent was removed by distillation under reduced pressure to obtain an oily product.

Separately, 122 mg of N-dodecanoyl-N-methylglycine was dissolved in 3 ml of anhydrous tetrahydrofuran, and to the solution were added 77 mg of 1-hydroxybenzotriazole and 103 mg of dicyclohexylcarbodiimide, followed by stirring on an ice bath. Thirty minutes later, the liquid temperature was returned to room temperature, and the stirring was continued for an additional 3 hours. The precipitated crystals were removed by filtration.

The above prepared oily substance was dissolved in 5 ml of anhydrous methylene chloride, and the filtrate was added thereto under ice-cooling. The temperature of the mixture was returned to room temperature, and the mixture was stirred at that temperature for 1.5 hours. The reaction mixture was diluted with chloroform, washed with 1N hydrochloric acid, dried over anhydrous sodium sulfate, and then distilled to remove the solvent. The residue was purified by silica gel column chromatography using, as an eluent, a 10:1 (v/v) mixture of chloroform and acetone, then a 50:1 (v/v) mixture of chloroform and methanol, and finally a 20:1 (v/v) mixture of chloroform and methanol to yield 445 mg of the entitled compound as an oily substance.

$[\alpha]_D^{25}$: +19.2° (c=1.0, chloroform)

3) Preparation of 2-phosphonoxyethyl
2-deoxy-6-O-(2-deoxy-3-O-(N-dodecanoylglycyl)-2-[(N-dodecanoyl-N-methylglycyl)amino]-4-O-phosphono-β-D-glucopyranosyl)-3-O-(N-dodecanoylglycyl)
-2-[(N-dodecanoyl-N-methylglycol)amino]-α-D-glucopyranoside In a mixture of 50 ml of tetrahydrofuran and 2.5 ml of water was dissolved 424 mg of the compound prepared in 2) above, and 0.2 g of platinum dioxide was added thereto, followed by stirring under hydrogen gas for 2 hours. The catalyst was removed by filtration, and the filter cake was washed with a 8:3:1 (v/v) mixture (lower layer) of chloroform, methanol, and water. The filtrate and the washing were combined, and the solvent was removed therefrom by distillation under reduced pressure. The residue was purified by thin layer chromatography using a 6:4:0.7 (v/v) mixture of chloroform, methanol, and water as a developing solvent, and then treated with a strongly acidic ion exchange resin, Dowex 50 (H+ type) produced by Dow Chemical Co., Ltd.). The solvent was removed by distillation under reduced pressure, and the residue was suspended in dioxane. Freeze-drying of the suspension gave 204 mg of the entitled compound as a white powder.

Melting Point: 165°-170° C. (gradually colored and turned to jelly)

$[\alpha]_D^{25}$: +4.6 [c=0.7, chloroform:methanol=3:1 (v/v)]

IR $\nu_{max}^{KBr}$cm$^{-1}$: 3400, 2930, 2850, 1750, 1675, 1650

NMR (CDCl$_3$—CD$_3$OD), δ(ppm): 0.90 (12H, t), 1.30 (s), 2.29 (4H, m), 2.44 (4H, t), 2.94 and 3.11 (total 6H, each s), 4.84 (1H, d), 5.18 (1H, m), 5.34 (1H, m)

A part of the resulting product was dissolved in a 3:1 (v/v) mixture of chloroform and methanol, and the solution was adjusted to a pH of about 9 with triethylamine, followed by concentration under reduced pressure. The residue was dissolved in a 0.1% triethylamine aqueous solution, followed by filtration through a millipore filter. The filtrate was freeze-dried to produce a triethylamine salt of the entitled compound as a white powder.

EXAMPLE 2

Preparation of
2-(diphenylphosphonoxy)ethyl-2-deoxy-6-O-[2-deoxy-4-O-diphenylphosphono-3-O-(N-dodecanoylglycyl)-6-O-(2,2,2-trichloroethoxycarbonyl)-2-(2,2,2-trichloroethoxycarbonylamino)-β-D-glucopyranosyl]-2-[6-(octanoylamino)hexanoylamino]-3-O-tetradecanoyl-α-D-glucopyranoside In the same manner as in Example 1-1), 445 mg of 1-O-acetyl-2-deoxy-4-O-diphenylphosphono-3-O-(N-dodecanoylglycyl)-6-O-(2,2,2-trichloroethoxycarbonyl)-2-(2,2,2-trichloroethoxycarbonylamino)-D-glycopyranose and 385 mg of 2-(diphenylphosphonoxy)ethyl-2-deoxy-2-[6-(octanoylamino)hexanoylamino]-3-O-tetradecanoyl-o-D-glucopyranoside were reacted to obtain 650 mg of the entitled compound as an oily substance.

$[\alpha]_D^{25}$: +22.2° (c=1.0, chloroform)

2) Preparation of 2-(diphenylphosphonoxy)ethyl
2-deoxy-6-O-[2-deoxy-4-O-diphenylphosphono-3-O-(N-dodecanoylglycyl)-2-tetradecanoylamino-β-D-glucopyranosyl]-2-[6-(octanoylamino)hexanoylamino]-3-O-tetradecanoyl-α-D-glucopyranoside In 10 ml of acetic acid was dissolved 620 mg of the compound prepared in 1) above, and 1.5 g of zinc powder was suspended therein, followed by stirring at room temperature for 3 hours. Any insoluble matter was removed by filtration, and solvent was removed by distillation under reduced pressure, and the residue was dissolved in chloroform. The solution was washed successively with 1N hydrochloric acid, water, a 5% sodium hydrogencarbonate aqueous solution, and water, and dried over anhydrous magnesium sulfate. The solvent was removed by concentration under reduced pressure, and the residue was dissolved in 10 ml of anhydrous tetrahydrofuran. To the solution were added 98 mg of tetradecanoic acid, 58 mg of 1-hydroxybenzotriazole, and 90 mg of dicyclohexylcarbodiimide under ice-cooling, and the liquid temperature was gradually elevated up to room temperature, followed by stirring for one night. The precipitated insoluble matter was removed by filtration, and the filtrate was concentrated under reduced pressure. The residual solid was purified by silica gel column chromatography using, as an eluent, a 10:1 (v/v) mixture of chloroform and acetone and then a 30:1 (v/v) mixture of chloroform and methanol, and then powderized from acetonitrile to obtain 428 mg of the entitled compound as a white powder.

Melting Point: 105°-107° C.

$[\alpha]_D^{25}$: +24.7° (c=1.0, chloroform)

3) Preparation of 2-phosphonoxyethyl 2-deoxy-6-O-[2-deoxy-4-O-phosphono-3-O-(N-dodecanoylglycyl)-2-tetradecanoylamino-β-D-glucopyranosyl]-2-[6-(octanoylamino)hexanoylamino]-3-O-tetradecanoyl-α-D-glucopyranoside In the same manner as in Example 1-3), 350 mg of the compound prepared in 2) above was reacted to obtain 162 mg of the entitled compound as a white powder.

Melting Point: 169°-172° C. (colored and turned to jelly)

$[\alpha]_D^{25}$: +19.5° [c=0.6, chloroform:methanol=3:1 (v/v)]

IR $\nu_{max}^{KBr}$cm$^{-1}$: 3405, 2925, 2855, 1740, 1645, 1560, 1460

NMR (CDCl$_3$), δ(ppm): 0.90 (12H, t), 1.30 (s), 2.1-2.4 (10H, m), 3.19 (2H, t), 5.17 (1H, t), 5.38 (1H, t)

The resulting compound was treated in the same manner as in Example 1-3) to obtain a triethylamine salt of the entitled compound as a white powder.

EXAMPLE 3

Preparation of 2-(diphenylphosphonoxy)ethyl 2-deoxy-6-O-[2-deoxy-4-O-diphenylphosphono-3-O-(4-oxotetradecanoyl-6-O-(2,2,2-trichloroethoxycarbonyl)-2-(2,2,2-trichloroethoxycarbonylamino)-β-D-glucopyranosyl]-3-O-(4-oxotetradecanoyl)-2-tetradecanoylamino-α-D-glucopyranoside In the same manner as in Example 1-1), 435 mg of 1-O-acetyl-2-deoxy-4-O-diphenylphosphono-3-O-(4-oxotetradecanoyl)-6-O-(2,2,2-trichloroethoxycarbonyl)-2-(2,2,2-trichloroethoxycarbonylamino)-D-glucopyranose and 380 mg of 2-(diphenylphosphonoxy)ethyl 2-deoxy-3-O-(4-oxotetradecanoyl)-2-tetradecanoylamino-α-D-glucopyranoside were reacted to obtain 516 mg of the entitled compound as an oily substance.

$[\alpha]_D^{25}$: +14.7° (c=0.03, chloroform)

2) Preparation of 2-(diphenylphosphonoxy)ethyl-2-deoxy-6-O-[2-deoxy-4-O-diphenylphosphono-3-O-(4-oxotetradecanoyl)-2-tetradecanoylamino-β-D-glucopyranosyl]-3-O-(4-oxotetradecanoyl)-2-tetradecanoylamino-α-D-glucopyranoside In 5 ml of acetic acid was dissolved 510 mg of the compound prepared in 1) above, and 0.5 g of zinc powder was suspended in the solution, followed by stirring at room temperature for 1.5 hours. The insoluble matter was removed by filtration, and the filtrate was distilled off under reduced pressure. The resulting residue was diluted with chloroform, washed successively with 1N hydrochloric acid, a 5% sodium hydrocarboncarbonate aqueous solution, and water, dried over anhydrous sodium sulfate, and distilled under reduced pressure to remove the solvent. The resulting oily substance was dissolved in 2 ml of anhydrous methylene chloride, and to the solution were added 88 mg of tetradecanoyl chloride and 2 ml of N-methylmorpholine under ice-cooling. The mixture was stirred at the same temperature for 30 minutes. The reaction mixture was diluted with chloroform, washed successively with 1N hydrochloric acid and water, and dried over anhydrous sodium sulfate. The solvent was removed by distillation under reduced pressure, and the residue was purified by silica gel column chromatography using, as an eluent, chloroform and then a 20:1 (v/v) mixture of chloroform and methanol to obtain 229 mg of the entitled compound as an oily substance.

$[\alpha]_D^{25}$: +17.° (c=0.2, chloroform)

3) Preparation of 2-phosphonoxyethyl-2-deoxy-6-O-[2-deoxy-4-O-phosphono-3-O-(4-oxotetradecanoyl)-2-tetradecanoylamino-β-D-glucopyranosyl]-3-O-(4-oxotetradecanoyl)-2-tetradecanoylamino-α-D-glucopyranoside In the same manner as in Example 1-3), 225 mg of the compound prepared in 2) above was reacted and treated to obtain 91 mg of the entitled compound as a white powder.

Melting point: 166°-170° C. (colored and jelly-like)

IR $\nu_{max}^{KBr}$cm$^{-1}$: 3406, 2926, 2854, 1710, 1662, 1557, 1470

NMR (CDCl$_3$—OD), δ(ppm): 0.88 (12H, t), 1.26 (s), 2.22 (4H, m), 2.54 (4H, t), 2.64 (4H, m), 2.76 (4H, m), 5.16 (1H, t), 5.30 (1H, t)

The resulting compound was treated in the same manner as in Example 1-3) to obtain a triethylamine salt thereof as a white powder.

EXAMPLE 4

Preparation of benzyloxycarbonylmethyl-2-deoxy-6-O-[2-deoxy-4-O-diphenylphosphono-3-O-(N-dodecanoylglycyl)-6-O-(2,2,2-trichloroethoxycarbonyl)-2-(2,2,2-trichloroethoxycarbonylamino)-β-D-glucopyranosyl]-3-O-tetradecanoyl-2-tetradecanoylamino-α-D-glucopyranoside In the same manner as in Example 1-1), 303 mg of 1-O-acetyl-2-deoxy-4-O-diphenylphosphono-3-O-(N-dodecanoylglycyl)-6-O-(2,2,2-trichloroethoxycarbonyl)-2-(2,2,2-trichloroethoxycarbonylamino)-D-glucopyranose and 217 mg of benzyloxycarbonylmethyl 2-deoxy-3-O-tetradecanoyl-2-tetradecanoylamino-α-D-glucopyranoside were reacted to obtain 408 mg of the entitled compound as an oily substance.

$[\alpha]_D^{25}$: +25.8° (c=1.0, chloroform)

2) Preparation of benzyloxycarbonylmethyl 2-deoxy-6-O-[2-deoxy-4-O-diphenylphosphono-3-O-(N-dodecanoylglycyl)-2-tetradecanoylamino-β-D-glucopyranosyl]-3-O-tetradecanoyl-2-tetradecanoylamino-α-D-glucopyranoside In the same manner as in Example 1-2), 389 mg of the compound prepared in 1) above was reacted with tetradecanoic acid to obtain 293 mg of the entitled compound as an oily substance.

$[\alpha]_D^{25}$: +28.4° (c=1.1, chloroform)

3) Preparation of carboxymethyl 2-deoxy-6-O-[2-deoxy-3-O-(N-dodecanoylglycyl)-4-O-phosphono-2-tetradecanoylamino-β-D-glucopyranosyl]-3-O-tetradecanoyl-2-tetradecanoylamino-α-D-glucopyranoside In a mixture of 40 ml of tetrahydrofuran and 1 ml of water was dissolved 278 mg of the compound prepared in 2) above, and 0.3 g of 5% palladium-on-carbon was added thereto, followed by stirring under hydrogen gas for 1 hour. Then, 150 mg of platinum dioxide was added thereto, and the stirring under hydrogen gas was continued for an additional 2.5 hours. The catalyst was filtered, and the filtrate was distilled to remove the solvent. The residue was purified by thin layer chromatography using, as a developing solvent, a lower layer of a 8:3:1 (v/v) mixture of chloroform, methanol, and water and then treated with a strongly acidic ion exchange resin, Dowex 50 (H+type). The active fraction was distilled to remove the solvent, and the residue was suspended in dioxane. The suspension was freeze-dried to obtain 68 mg of the entitled compound as a white powder.

Melting Point: 150°-155° C. (colored and jelly-like)
IR $\nu_{max}^{KBr}$cm$^{-1}$: 3400, 2925, 2855, 1745, 1650, 1470
NMR (CDCl$_3$), δ(ppm): 0.90 (12H, t), 1.30 (s), 2.1-2.4 (8H, m), 4.82 (2H, m), 5.22 (1H, t), 5.37 (1H, t)

EXAMPLE 5

1) Preparation of allyl 2-deoxy-6-O-[2-deoxy-4-O-diphenylphosphono-3-O-(N-dodecanoylglycyl)-6-O-(2,2,2-trichloroethoxycarbonyl)-2-(2,2,2-trichloroethoxycarbonylamino)-β-D-glucopyranosyl]-3-O-tetradecanoyl-2-tetradecanoylamino-α-D-glucopyranoside In the same manner as in Example 1-1), 2.00 g of 1-O-acetyl-2-deoxy-4-O-diphenylphosphono-3-O-(N-dodecanoylglycyl)-6-O-(2,2,2-trichloroethoxycarbonyl)-2-(2,2,2-trichloroethoxycarbonylamino)-D-glucopyranose and 1.23 g of allyl 2-deoxy-3-O-tetradecanoyl-2-tetradecanoylamino-α-D-glucopyranoside to obtain 2.65 g of the entitled compound as a caramel-like substance.

$[α]_D^{25}$: +27.2° (c=1.4, chloroform)

2) Preparation of allyl 2-deoxy-6-O-[2-deoxy-4-O-diphenylphosphono-3-O-(N-dodecanoylglycyl;-2-tetradecanoylamino-β-D-glucopyranosyl]-3-O-tetradecanoyl-2-tetradecanoylamino-α-D-glucopyranoside In the same manner as in Example 1-2), 2.65 g of the compound prepared in 1) above was reacted with tetradecanoic acid to obtain 2.25 g of the entitled compound as a caramel-like substance.

$[α]_D^{25}$: +21.8° (c=0.9, chloroform)

3) Preparation of allyl 6-O-[6-O-benzyloxymethyl-2-deoxy-4-O-diphenylphosphono-3-O-(N-dodecanoylglycyl)-2-tetradecanoylamino-β-D-glucopyranosyl]-2-deoxy-3-O-tetradecanoyl-2-tetradecanoylamino-α-D-glucopyranoside In 25 ml of anhydrous methylene chloride was dissolved 870 mg of the compound prepared in 2) above, and 0.82 ml of benzyloxymethyl chloride and 1.00 ml of diisopropylethylamine were added thereto, followed by stirring at room temperature for one night. To the mixture were further added 0.16 ml of benzyloxymethyl chloride and 0.20 ml of diisopropylethylamine, and the mixture was stirred for an additional 3 hours. The reaction mixture was washed successively with 1N hydrochloric acid, a 5% sodium hydrogencarbonate aqueous solution, and water. The organic layer was dried over anhydrous magnesium sulfate. The solvent was removed therefrom by distillation under reduced pressure, and acetone was added to the residue. The precipitated white powder was collected by filtration. The powder was dissolved in chloroform, subjected to silica gel column chromatography using, as an eluent, a 10:1 (v/v) mixture of chloroform and ethyl acetate, then a 5:1 (v/v) mixture of chloroform and ethyl acetate, and finally a 20:1 (v/v) mixture of chloroform and acetone, and powderized from acetonitrile to obtain 505 mg of the entitled compound as a white powder.

Melting Point: 154°-157° C.
$[α]_D^{25}$: +32.4° (c=1.2, chloroform)

4) Preparation of 6-O-benzyloxymethyl-2-deoxy-4-O-diphenylphosphono-3-O-(N-dodecanoylglycyl)-2-tetradecanoylamino-β-D-glucopyranosyl]-2-deoxy-3-O-tetradecanoyl-2-tetradecanoylamino-D-glucopyranose In 15 ml of anhydrous tetrahydrofuran was dissolved 480 mg of the compound prepared in 3) above. After the atmosphere was evacuated and displaced with nitrogen gas, 10 mg of 1,5-cyclooctadienebis(methyldiphenylphosphine)iridium hexafluorophosphate was added to the solution. The system was again evacuated to displace the air with nitrogen gas, and the atmosphere was further displaced with hydrogen gas. When the red color of the iridium complex disappeared, the atmosphere was again displaced with nitrogen, and the mixture was stirred for 2.5 hours while maintaining the temperature at 50° C. After allowing the reaction mixture to cool, 5 ml of water and then 180 mg of iodine were added thereto, followed by stirring at room temperature for 20 minutes. A 5% sodium thiosulfate aqueous solution was added to the reaction mixture until the color of iodine disappeared. The reaction mixture was extracted with chloroform, and the organic layer was separated, washed with water, and dried over anhydrous magnesium sulfate. The solvent was removed by distillation under reduced pressure, and the residue was purified by silica gel column chromatography using a 10:1 (v/v) mixture of chloroform and acetone and then a 50:1 (v/v) mixture of chloroform and methanol as an eluent, and powderized from acetonitrile to obtain 320 mg of the entitled compound as a white powder.

Melting Point: 155°-156° C.
$[α]_D^{25}$: +17.1° (c=0.7, chloroform)

5) Preparation of 2-deoxy-6-O-[2-deoxy-3-O-(N-dodecanoylglycyl)-4-O-phosphono-2-tetradecanoylamino-β-D-glucopyranosyl]-1-O-phosphono-3-O-tetradecanoyl-2-tetradecanoylamino-α-D-glucopyranose In 15 ml of anhydrous tetrahydrofuran was dissolved 170 mg of the compound prepared in 4) above. After displacing the atmosphere with nitrogen, a hexane solution containing 0.16 mmol of n-butyl lithium was added thereto under cooling to about −70° C. Five minutes later, a benzene solution containing 0.16 mmol of dibenzylphosphorochloridate was added thereto, followed by stirring at −50° C. for 30 minutes. To the reaction mixture were added 100 mg of palladium black and 85 mg of 5% palladium-on-carbon, followed by stirring under a hydrogen stream overnight. The catalyst was separated by filtration, and the filtrate was distilled under reduced pressure. The resulting residue was dissolved in 150 ml of tetrahydrofuran, and 0.27 9 of platinum dioxide was added to the solution. The mixture was stirred for 4 hours under a hydrogen stream, followed by filtration to separate the catalyst. The filtrate was distilled under reduced pressure to remove the solvent, and the residue was purified by thin layer chromatography using a 6:4:1 (v/v) mixture of chloroform, methanol, and water as a developing solvent and then treated with a strongly acidic ion exchange resin, Dowex 50 (H+type). To the resulting fraction was added 40 μl of triethylamine, followed by distillation under reduced pressure. The residue was suspended in dioxane, and the suspension was freeze-dried to obtain 38 mg of a triethylamine salt of the entitled compound as a white powder.

Melting Point: 148°-150° C. (colored and jelly-like)
$[\alpha]_D^{25}$: +10.1° [c=0.6, chloroform:methanol=3:1 (v/v)]
IR $\nu_{max}^{KBr}$cm$^{-1}$: 3400, 2925, 2855, 2680, 2500, 1745, 1645, 1550, 1470, 1385, 1040
NMR (CDCl$_3$—CD$_3$OD), δ(ppm): 0.90 (12H, t), 1.28 (s), 2.1-2.5 (8H, m), 3.1-3.3 (12H, br)

EXAMPLE 6

1) Preparation of 2-(diphenylphosphonoxy)ethyl 2-deoxy-6-[2-deoxy-4-O-diphenylphosphono-3-O-(N-dodecanoylglycyl)-6-O-(2,2,2-trichloroethoxycarbonyl)-2-(2,2,2-trichloroethoxycarbonylamino)-β-D-glucopyranosyl]-4-O-diphenylphosphono-3-O-(N-dodecanoylglycyl)-2-[(N-dodecanoyl-N-methylglycyl)amino]-α-D-glucopyranoside -) In 5 ml of anhydrous methylene chloride was dissolved 500 mg of the compound prepared in Example 1-1), and 0.04 ml of pyridine, 139 mg of diphenylphosphorochloridate, and 64 mg of 4-dimethylaminopyridine were added thereto in this order at room temperature, followed by stirring overnight. The reaction mixture was diluted with methylene chloride, washed successively with a 10% hydrochloric acid aqueous solution, a saturated sodium hydrogencarbonate aqueous solution, and a saturated sodium chloride aqueous solution, and dried over anhydrous magnesium sulfate. The solvent was removed therefrom by distillation under reduced pressure, and the residue was purified by silica gel column chromatography using a 40:1 (v/v) mixture of chloroform and methanol as an eluent to obtain 368 mg of the entitled compound as an oily substance.

$[\alpha]_D^{25}$: +21.9° (c=0.8, chloroform)

2) Preparation of 2-(diphenylphosphonoxy)ethyl-2-deoxy-6-O-(2-deoxy-4-O-diphenylphosphono)-3-O-(N-dodecanoylglycyl)-2-[N-dodecanoyl-N-methylglycyl)amino]-β-D-glucopyranosyl)-4-O-diphenylphosphono-3-O-(N-dodecanoylglycyl)-2-[(N-dodecanoyl-N-methylglycyl)amino]-α-D-glucopyranoside In the same manner as in Example 1-2), 350 mg of the compound obtained in 1) above was treated with zinc powder in an acetic acid solution and then reacted with N-dodecanoyl-N-methylglycine to obtain 244 mg of the entitled compound as an oily substance.

$[\alpha]_D^{25}$: +3.5° (c=0.6, chloroform)

3) Preparation of 2-phosphonoxyethyl-2-deoxy-6-O-(2-deoxy-3-O-(N-dodecanoylglycyl)-2-[(N-dodecanoyl-N-methylglycyl)amino]-4-O-phosphono-β-glucopyranosyl)-3-O-(N-dodecanoylglycyl)-2-[(N-dodecanoyl-N-methylglycyl)amino]-4-O-phosphono-α-D-glucopyranoside In the same manner as in Example 1-3), 238 mg of the compound prepared in 2) above was subjected to catalytic reduction to obtain 101 mg of the entitled compound as a white powder.

Melting Point: 184°-189° C. (colored and jelly-like)
$[\alpha]_D^{25}$: −24.3° [c=0.6, chloroform:methanol=3:1 (v/v)]
IR $\nu_{max}^{KBr}$cm$^{-1}$: 3280, 2900, 1740, 1660, 1640
NMR (CDCl$_3$—CD$_3$OD), δ(ppm): 0.89 (12H, t, J=7.0Hz), 1.28 (brs), 1.62 (8H, br), 2.24-2.31 (4H, m), 2.40-2.42 (4H, m), 2.91-2.96, 3.09, 3.12 (total 6H, each s), 4.84 (1H, d), 5.19 (1H, t), 5.31 (1H, t)

EXAMPLE 7

1) Preparation of 2-(diphenylphosphonoxy)ethyl 3-O-[(R)-3-benzyloxytetradecanoyl]-2-[(R)-3-benzyloxytetradecanoylamino]-2-deoxy-6-O-(2-deoxy-4-O-diphenylphosphono-6-O-(2,2,2-trichloroethoxycarbonyl)-2-(2,2,2-trichloroethoxycarbonylamino)-3-O-[(R)-3-(2,2,2-trichloroethoxycarbonyloxy)tetradecanoyl]-β-D-glucopyranosyl)-α-D-glucopyranoside In the same manner as in Example 1-1), 409 mg of 1-O-acetyl-2-deoxy-4-O-diphenylphosphono-6-O-(2,2,2-trichloroethoxycarbonyl)-2-(2,2,2-trichloroethoxycarbonylamino)-3-O-[(R)-3-(2,2,2-trichloroethoxycarbonyloxy)tetradecanoyl]-D-glucopyranose was reacted with hydrogen bromide to obtain an oily substance, and the resulting oily substance was reacted with 370 mg of 2-(diphenylphosphonoxy)ethyl 3-O-[(R)-3-benzyloxytetradecanoyl]-2-[(R)-3-benzyloxytetradecanoylamino]-2-deoxy-α-D-glucopyranoside in the presence of mercury (II) cyanide to obtain 577 mg of the entitled compound as a pale yellow, viscous oily substance.

$[\alpha]_D^{25}$: +20.2° (c=0.2, chloroform)

2) Preparation of 2-(diphenylphosphonoxy)ethyl 3-O-[(R)-3-benzyloxytetradecanoyl]-2-[(R)-3-benzyloxytetradecanoylamino]-2-deoxy-6-O-(2-deoxy-4-O-diphenylphosphono-3-O-[(R)-3-hydroxytetradecanoyl]-2-[(R)-3-hydroxytetradecanoylamino]-β-D-glucopyranosyl)-α-D-glucopyranoside In the same manner as in Example 1-2), 555 mg of the compound prepared in 1) above was treated with a zinc powder in an acetic acid solution, and the reaction product was reacted with 93 mg of (R)-3-hydroxytetradecanoic acid to obtain 312 mg of the entitled compound as a colorless oily substance.

$[\alpha]_D^{25}$: +6.3° (c=0.7, chloroform)

3) Preparation of 2-phosphonoxyethyl 2-deoxy-6-O-(2-deoxy-3-O-[(R)-3-hydroxytetradecanoyl]-2-[(R)-3-hydroxytetradecanoylamino]-4-O-phosphono-β-D-glucopyranosyl)-3-O-[(R)-3-hydroxytetradecanoyl]-2-[(R)-3-hydroxytetradecanoylamino]-α-D-glucopyranoside In the same manner as in Example 4-3), 294 mg of the compound prepared in 2) above was catalytically reduced in the presence of a 5% palladium-on-carbon catalyst to obtain the entitled compound. The compound was treated with a 0.1% triethylamine aqueous solution to obtain 76 mg of a triethylamine salt of the entitled compound as a white powder. A part of the product was treated with a strongly acidic ion exchange resin to obtain the entitled compound in a free form as a white powder.

The following data are of the free compound.

$[\alpha]_D^{25}$: −1.8° [c=0.5, chloroform:methanol=3:1 (v/v)]

Melting Point: 155°–158° C. (colored and jelly-like)

IR $\nu_{max}^{KBr}$cm$^{-1}$: 3440, 2930, 2860, 1740, 1660

NMR (CDCl$_3$—CD$_3$OD), δ(ppm): 0.90 (12H, t), 2.3–2.5 (8H, m), 5.2 (2H, m)

EXAMPLE 8

1) Preparation of 2-(diphenylphosphonoxy)ethyl 4-O-[3-(benzyloxycarbonyl)propionyl]-2-deoxy-6-O-[2-deoxy-4-O-diphenylphosphono-3-O-(N-dodecanoylglycyl)-6-O-(2,2,2-trichloroethoxycarbonyl)-2-(2,2,2-trichloroethoxycarbonylamino)-β-D-glucopyranosyl]-3-O-(N-dodecanoylglycyl)-2-tetradecanoylamino-α-D-glucopyranoside In 6 ml of anhydrous methylene chloride was dissolved 483 mg of 2-(diphenylphosphonoxy)ethyl 2-deoxy-6-O-[2-deoxy-4-O-diphenylphosphono-3-O-(N-dodecanoylglycyl)-6-O-(2,2,2-trichloroethoxycarbonyl)-2-(2,2,2-trichloroethoxycarbonylamino)-β-D-glucopyranosyl]-3-O-(N-dodecanoylglycyl)-2-tetradecanoylamino-α-D-glucopyranoside, and 108 mg of monobenzyl succinate and 16 mg of of dimethylaminopyridine were added to the solution. To the solution was added 107 mg of dicyclohexylcarbodiimide under ice-cooling. The liquid temperature was returned to room temperature, and the mixture was stirred for 1 hour. The insoluble matter was removed by filtration, and the filtrate was washed with 1N hydrochloric acid, and dried over anhydrous sodium sulfate. The solvent was removed by distillation under reduced pressure, and the residue was purified by silica gel column chromatography using, as an eluent, 10% acetone-containing chloroform and then 3% methanol-containing chloroform to obtain 113 mg of the entitled compound as an oily substance.

$[\alpha]_D^{25}$: +35.6° (c=1.1, chloroform)

2) Preparation of 2-(diphenylphosphonoxy)ethyl 4-O-[3-(benzyloxycarbonyl)propionyl-2-deoxy-6-O-[2-deoxy-4-O-diphenylphosphono-3-O-(N-dodecanoylglycyl)-2-tetradecanoylamino-β-D-glucopyranosyl]-3-O-(N-dodecanoylglycyl)-2-tetradecanoylamino-α-D-glucopyranoside In the same manner as in Example 1-2), 327 mg of the compound prepared in 1) above was treated with zinc powder in an acetic acid solution, and the product was reacted with tetradecanoic acid to obtain 226 mg of the entitled compound an oily substance.

$[\alpha]_D^{25}$: +29.6° (c=1.2, chloroform)

3) Preparation of 2-phosphonoxyethyl 4-O-(3-carboxypropionyl)-2-deoxy-6-O-[2-deoxy 3-O-(N-dodecanoylglycyl)-4-O-phosphono-2-tetradecanoylamino-β-D-glucopyranosyl]-3-O-(N-dodecanoylglycyl)-2-tetradecanoylamino-α-D-glucopyranoside In the same manner as in Example 4-3), 204 mg of the compound prepared in 2) above was reacted to obtain 97 mg of the entitled compound as a white powder.

Melting Point: 150°–155° C. (colored and jelly-like)

$[\alpha]_D^{25}$: +24.4° (c=0.5, chloroform:methanol=3:1 (v/v))

IR $\nu_{max}^{KBr}$cm$^{-1}$: 3300, 2925, 2855, 1755, 1660, 1555

NMR (CDCl$_3$—CD$_3$OD), δ(ppm): 0.89 (12H, t), 1.27 (s), 2.2–2.3 (8H, m), 2.6–2.7 (4H, m), 4.18 (2H, m), 4.27 (2H, m), 4.61 (1H, d), 4.82 (1H, d), 5.06 (1H, t), 5.24 (1H, t), 5.30 (1H, t)

EXAMPLES 9 TO 81

In the same manner as described in Examples 1 to 8, the following compounds represented by formula (Ia) were prepared.

(Ia)

| Example No. | R⁴ | R³ | R² | R¹ |
|---|---|---|---|---|
| 9 | —COCH$_2$NHCO(CH$_2$)$_{10}$CH$_3$ | —CO(CH$_2$)$_{12}$CH$_3$ | —COCH$_2$NHCO(CH$_2$)$_{10}$CH$_3$ | —CO(CH$_2$)$_{12}$CH$_3$ |
| 10 | —CO(CH$_2$)$_2$CO(CH$_2$)$_9$CH$_3$ | CH$_3$<br>\|<br>—COCH$_2$NCO(CH$_2$)$_{10}$CH$_3$ | —COCH$_2$NHCO(CH$_2$)$_{10}$CH$_3$ | CH$_3$<br>\|<br>—COCH$_2$NCO(CH$_2$)$_{10}$CH$_3$ |
| 11 | —CO(CH$_2$)$_2$CO(CH$_2$)$_9$CH$_3$ | —CO(CH$_2$)$_{12}$CH$_3$ | —COCH$_2$NHCO(CH$_2$)$_{10}$CH$_3$ | —CO(CH$_2$)$_{12}$CH$_3$ |
| 12 | —CO(CH$_2$)$_2$NHCO(CH$_2$)$_9$CH$_3$ | —CO(CH$_2$)$_{12}$CH$_3$ | —CO(CH$_2$)$_5$NHCO(CH$_2$)$_6$CH$_3$ | —CO(CH$_2$)$_5$NHCO(CH$_2$)$_6$CH$_3$ |
| 13 | —COCH$_2$NHCO(CH$_2$)$_{10}$CH$_3$ | —CO(CH$_2$)$_{12}$CH$_3$ | —CO(CH$_2$)$_2$NHCO(CH$_2$)$_4$CH$_3$ | —CO(CH$_2$)$_2$NHCO(CH$_2$)$_4$CH$_3$ |
| 14 | —COCH$_2$NHCO(CH$_2$)$_{10}$CH$_3$ | —COCH$_2$NHCO(CH$_2$)$_{10}$CH$_3$ | —COCH$_2$NHCO(CH$_2$)$_{10}$CH$_3$ | —COCH$_2$NHCO(CH$_2$)$_{10}$CH$_3$ |
| 15 | CH$_3$  CH$_3$<br>\|<br>—COCH—NCO(CH$_2$)$_9$CH$_3$ | —CO(CH$_2$)$_{12}$CH$_3$ | CH$_3$  CH$_3$<br>\|<br>—COCH—NCO(CH$_2$)$_9$CH$_3$ | —CO(CH$_2$)$_{12}$CH$_3$ |
| 16 | —CO(CH$_2$)$_2$CO(CH$_2$)$_9$CH$_3$ | CH$_3$<br>\|<br>—COCH$_2$NCO(CH$_2$)$_{10}$CH$_3$ | —CO(CH$_2$)$_2$CO(CH$_2$)$_9$CH$_3$ | CH$_3$<br>\|<br>—COCH$_2$NCO(CH$_2$)$_{10}$CH$_3$ |
| 17 | —COCH$_2$NHCO(CH$_2$)$_{10}$CH$_3$ | —COCH$_2$NHCO(CH$_2$)$_{10}$CH$_3$ | —COCH$_2$NHCO(CH$_2$)$_{10}$CH$_3$ | —COCH$_2$NHCO(CH$_2$)$_{10}$CH$_3$ |
| 18 | CH$_3$<br>\|<br>—COCHNHCO(CH$_2$)$_{10}$CH$_3$ | CH$_3$<br>\|<br>—COCHNHCO(CH$_2$)$_{10}$CH$_3$ | CH$_3$<br>\|<br>—COCHNHCO(CH$_2$)$_{10}$CH$_3$ | CH$_3$<br>\|<br>—COCHNHCO(CH$_2$)$_{10}$CH$_3$ |
| 19 | —COCH$_2$NHCO(CH$_2$)$_{10}$CH$_3$ | —COCH$_2$NHCO(CH$_2$)$_{10}$CH$_3$ | —COCH$_2$NHCO(CH$_2$)$_{10}$CH$_3$ | —COCH$_2$OCO(CH$_2$)$_{10}$CH$_3$ |
| 20 | —CO(CH$_2$)$_5$NHCO(CH$_2$)$_6$CH$_3$ | —CO(CH$_2$)$_5$NHCO(CH$_2$)$_6$CH$_3$ | —CO(CH$_2$)$_5$NHCO(CH$_2$)$_8$CH$_3$ | —CO(CH$_2$)$_5$NHCO(CH$_2$)$_6$CH$_3$ |
| 21 | —CO(CH$_2$)$_2$NHCO(CH$_2$)$_8$CH$_3$ | —CO(CH$_2$)$_{12}$CH$_3$ | —CO(CH$_2$)$_2$NHCO(CH$_2$)$_8$CH$_3$ | —CO(CH$_2$)$_{12}$CH$_3$ |
| 22 | —CO(CH$_2$)$_2$CO(CH$_2$)$_9$CH$_3$ | —CO(CH$_2$)$_{12}$CH$_3$ | —CO(CH$_2$)$_2$CO(CH$_2$)$_9$CH$_3$ | —CO(CH$_2$)$_2$CO(CH$_2$)$_9$CH$_3$ |
| 23 | —COCH$_2$NHCO(CH$_2$)$_{10}$CH$_3$ | —CO(CH$_2$)$_{10}$CH$_3$ | —COCH$_2$NHCO(CH$_2$)$_{10}$CH$_3$ | —CO(CH$_2$)$_{10}$CH$_3$ |
| 24 | —COCH$_2$NHCO(CH$_2$)$_{10}$CH$_3$ | —CO(CH$_2$)$_2$CO(CH$_2$)$_2$NHCO—<br>(CH$_2$)$_6$CH$_3$ | —COCH$_2$NHCO(CH$_2$)$_{10}$CH$_3$ | —CO(CH$_2$)$_2$CO(CH$_2$)$_2$NHCO—<br>(CH$_2$)$_6$CH$_3$ |
| 25 | CH$_3$<br>\|<br>—COCH$_2$NCO(CH$_2$)$_{10}$CH$_3$ | —CO(CH$_2$)$_{12}$CH$_3$ | CH$_3$<br>\|<br>—COCH$_2$NCO(CH$_2$)$_{10}$CH$_3$ | —CO(CH$_2$)$_{12}$CH$_3$ |
| 26 | —CO(CH$_2$)$_{12}$CH$_3$ | —CO(CH$_2$)$_{12}$CH$_3$ | —CO(CH$_2$)$_{12}$CH$_3$ | —CO(CH$_2$)$_{12}$CH$_3$ |
| 27 | —CO(CH$_2$)$_5$NHCO(CH$_2$)$_6$CH$_3$ | —CO(CH$_2$)$_{12}$CH$_3$ | —CO(CH$_2$)$_5$NHCO(CH$_2$)$_6$CH$_3$ | —CO(CH$_2$)$_{12}$CH$_3$ |

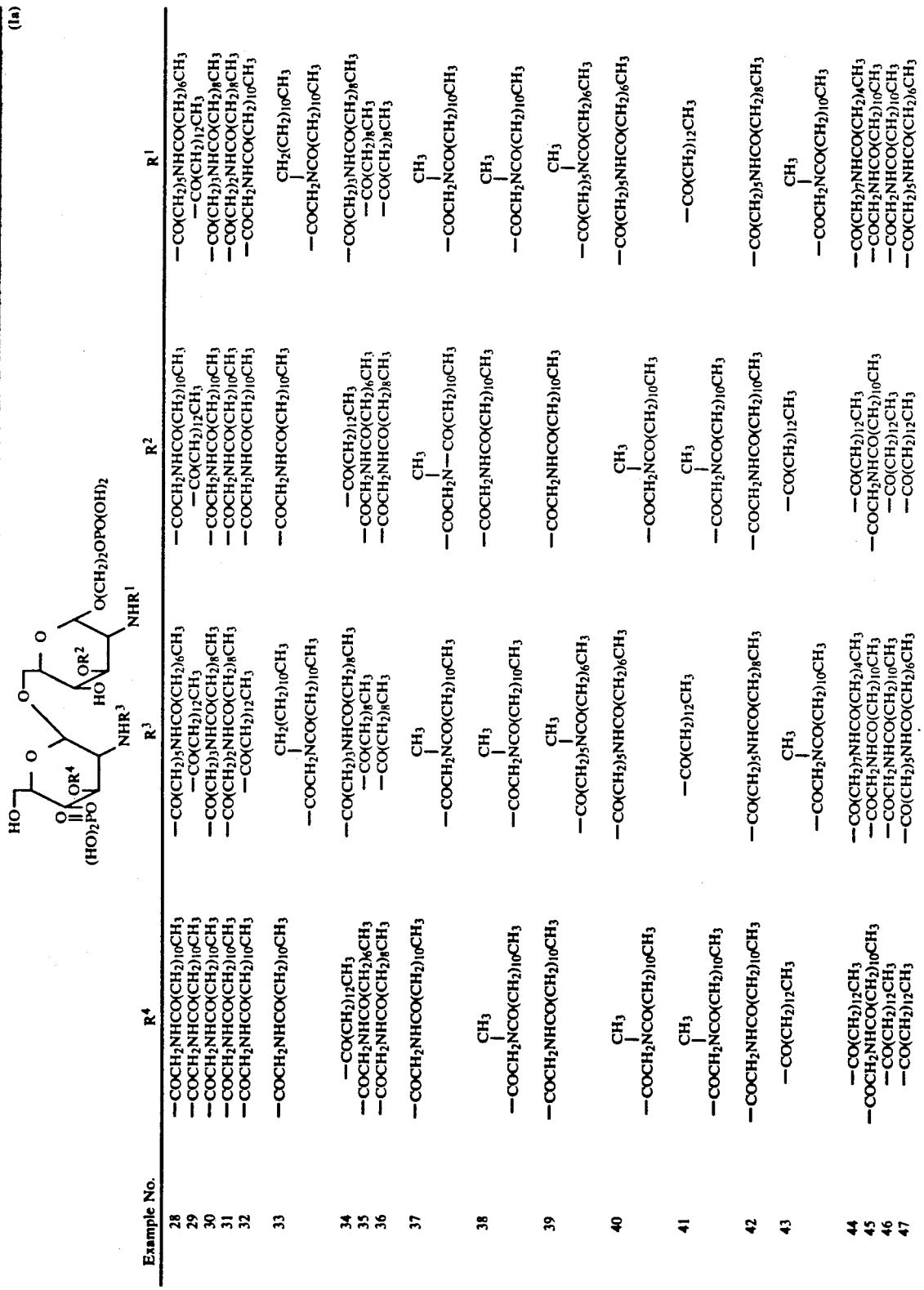

(Ia)

| Example No. | $R^4$ | $R^3$ | $R^2$ | $R^1$ |
|---|---|---|---|---|
| 28 | —COCH$_2$NHCO(CH$_2$)$_{10}$CH$_3$ | —CO(CH$_2$)$_5$NHCO(CH$_2$)$_6$CH$_3$ | —COCH$_2$NHCO(CH$_2$)$_{10}$CH$_3$ | —CO(CH$_2$)$_5$NHCO(CH$_2$)$_6$CH$_3$ |
| 29 | —COCH$_2$NHCO(CH$_2$)$_{10}$CH$_3$ | —CO(CH$_2$)$_{12}$CH$_3$ | —COCH$_2$NHCO(CH$_2$)$_{10}$CH$_3$ | —CO(CH$_2$)$_{12}$CH$_3$ |
| 30 | —COCH$_2$NHCO(CH$_2$)$_{10}$CH$_3$ | —CO(CH$_2$)$_3$NHCO(CH$_2$)$_8$CH$_3$ | —COCH$_2$NHCO(CH$_2$)$_{10}$CH$_3$ | —CO(CH$_2$)$_3$NHCO(CH$_2$)$_8$CH$_3$ |
| 31 | —COCH$_2$NHCO(CH$_2$)$_{10}$CH$_3$ | —COCH$_2$NHCO(CH$_2$)$_8$CH$_3$ | —COCH$_2$NHCO(CH$_2$)$_{10}$CH$_3$ | —COCH$_2$NHCO(CH$_2$)$_8$CH$_3$ |
| 32 | —COCH$_2$NHCO(CH$_2$)$_{10}$CH$_3$ | —CO(CH$_2$)$_{12}$CH$_3$ | —COCH$_2$NHCO(CH$_2$)$_{10}$CH$_3$ | —COCH$_2$NHCO(CH$_2$)$_{10}$CH$_3$ |
| 33 | —COCH$_2$NHCO(CH$_2$)$_{10}$CH$_3$ | CH$_2$(CH$_2$)$_{10}$CH$_3$<br>—COCH$_2$NCO(CH$_2$)$_{10}$CH$_3$ | —COCH$_2$NHCO(CH$_2$)$_{10}$CH$_3$ | CH$_2$(CH$_2$)$_{10}$CH$_3$<br>—COCH$_2$NCO(CH$_2$)$_{10}$CH$_3$ |
| 34 | —CO(CH$_2$)$_{12}$CH$_3$ | —CO(CH$_2$)$_3$NHCO(CH$_2$)$_8$CH$_3$ | —CO(CH$_2$)$_{12}$CH$_3$ | —CO(CH$_2$)$_3$NHCO(CH$_2$)$_8$CH$_3$ |
| 35 | —COCH$_2$NHCO(CH$_2$)$_6$CH$_3$ | —CO(CH$_2$)$_8$CH$_3$ | —COCH$_2$NHCO(CH$_2$)$_8$CH$_3$ | —CO(CH$_2$)$_8$CH$_3$ |
| 36 | —COCH$_2$NHCO(CH$_2$)$_8$CH$_3$ | —CO(CH$_2$)$_8$CH$_3$ | —COCH$_2$NHCO(CH$_2$)$_8$CH$_3$ | —CO(CH$_2$)$_8$CH$_3$ |
| 37 | —COCH$_2$NHCO(CH$_2$)$_{10}$CH$_3$ | CH$_3$<br>—COCH$_2$N—CO(CH$_2$)$_{10}$CH$_3$ | CH$_3$<br>—COCH$_2$N—CO(CH$_2$)$_{10}$CH$_3$ | CH$_3$<br>—COCH$_2$N—CO(CH$_2$)$_{10}$CH$_3$ |
| 38 | CH$_3$<br>—COCH$_2$NCO(CH$_2$)$_{10}$CH$_3$ | CH$_3$<br>—COCH$_2$NCO(CH$_2$)$_{10}$CH$_3$ | —COCH$_2$NHCO(CH$_2$)$_{10}$CH$_3$ | CH$_3$<br>—COCH$_2$NCO(CH$_2$)$_{10}$CH$_3$ |
| 39 | —COCH$_2$NHCO(CH$_2$)$_{10}$CH$_3$ | —CO(CH$_2$)$_5$NHCO(CH$_2$)$_6$CH$_3$ | —COCH$_2$NHCO(CH$_2$)$_{10}$CH$_3$ | —CO(CH$_2$)$_5$NHCO(CH$_2$)$_6$CH$_3$ |
| 40 | CH$_3$<br>—COCH$_2$NCO(CH$_2$)$_{10}$CH$_3$ | —CO(CH$_2$)$_5$NHCO(CH$_2$)$_6$CH$_3$ | CH$_3$<br>—COCH$_2$NCO(CH$_2$)$_{10}$CH$_3$ | —CO(CH$_2$)$_5$NHCO(CH$_2$)$_6$CH$_3$ |
| 41 | CH$_3$<br>—COCH$_2$NCO(CH$_2$)$_{10}$CH$_3$ | —CO(CH$_2$)$_{12}$CH$_3$ | —COCH$_2$NHCO(CH$_2$)$_{10}$CH$_3$ | —CO(CH$_2$)$_{12}$CH$_3$ |
| 42 | —CO(CH$_2$)$_{12}$CH$_3$ | —COCH$_2$NHCO(CH$_2$)$_8$CH$_3$ | —CO(CH$_2$)$_{12}$CH$_3$ | —COCH$_2$NHCO(CH$_2$)$_8$CH$_3$ |
| 43 | —COCH$_2$NHCO(CH$_2$)$_{10}$CH$_3$ | CH$_3$<br>—COCH$_2$NCO(CH$_2$)$_{10}$CH$_3$ | —COCH$_2$NHCO(CH$_2$)$_{10}$CH$_3$ | CH$_3$<br>—COCH$_2$NCO(CH$_2$)$_{10}$CH$_3$ |
| 44 | —CO(CH$_2$)$_{12}$CH$_3$ | —CO(CH$_2$)$_7$NHCO(CH$_2$)$_4$CH$_3$ | —CO(CH$_2$)$_{12}$CH$_3$ | —CO(CH$_2$)$_7$NHCO(CH$_2$)$_4$CH$_3$ |
| 45 | —COCH$_2$NHCO(CH$_2$)$_{10}$CH$_3$ | —COCH$_2$NHCO(CH$_2$)$_{10}$CH$_3$ | —COCH$_2$NHCO(CH$_2$)$_{10}$CH$_3$ | —COCH$_2$NHCO(CH$_2$)$_{10}$CH$_3$ |
| 46 | —CO(CH$_2$)$_{12}$CH$_3$ | —CO(CH$_2$)$_6$CH$_3$ | —CO(CH$_2$)$_{12}$CH$_3$ | —CO(CH$_2$)$_6$CH$_3$ |
| 47 | —CO(CH$_2$)$_{12}$CH$_3$ | —CO(CH$_2$)$_5$NHCO(CH$_2$)$_6$CH$_3$ | —CO(CH$_2$)$_{12}$CH$_3$ | —CO(CH$_2$)$_5$NHCO(CH$_2$)$_6$CH$_3$ |

-continued $$\begin{array}{c} \text{structure (Ia): disaccharide with } (HO)_2PO\text{-O- on one sugar, } OR^4, NHR^3, OR^2, NHR^1, \text{ and } O(CH_2)_2OPO(OH)_2 \end{array}$$

| Example No. | R⁴ | R³ | R² | R¹ |
|---|---|---|---|---|
| 48 | —CO(CH₂)₁₂CH₃ | COOH | —CO(CH₂)₁₂CH₃ | COOH |
| 49 | —CO(CH₂)₁₂CH₃ | —CO(CH₂)₂CHNHCO(CH₂)₈CH₃ | —CO(CH₂)₁₂CH₃ | —CO(CH₂)₂CHNHCO(CH₂)₈CH₃ |
| 50 | —CO(CH₂)₁₂CH₃ | CONH₂<br>—CO(CH₂)₂CHNHCO(CH₂)₈CH₃ | —CO(CH₂)₁₂CH₃ | CONH₂<br>—CH(CH₂)₂CHNHCO(CH₂)₈CH₃ |
| 51 | —CO(CH₂)₁₂CH₃ | —COCH₂-cyclohexyl | —CO(CH₂)₁₂CH₃ | —COCH₂-cyclohexyl |
|  |  | —COCH₂NHCOCH₂-cyclohexyl |  | —COCH₂NHCOCH₂-cyclohexyl |
| 52 | —COCH₂NHCO(CH₂)₁₀CH₃ | —COCH₂NHCO(CH₂)₁₀CH₃ | —COCH₂NHCO(CH₂)₁₀CH₃ | —CO(CH₂)₁₂CH₃ |
| 53 | —COCH₂NHCO(CH₂)₈CH₃ | —CO(CH₂)₂CO(CH₂)₉CH₃ | —COCH₂NHCO(CH₂)₉CH₃ | —CO(CH₂)₂CO(CH₂)₉CH₃ |
| 54 | —COCH₂NHCO(CH₂)₁₀CH₃ | —CO(CH₂)₁₂CH₃ | —COCH₂NHCO(CH₂)₆CH₃ | —COCH₂NHCO(CH₂)₆CH₃ |
| 55 | —COCH₂NHCO(CH₂)₁₀CH₃ | CH₃<br>—COCH₂NCO(CH₂)₁₀CH₃ | —CO(CH₂)₂CO(CH₂)₉CH₃ | CH₃<br>—COCH₂NCO(CH₂)₁₀CH₃ |
| 56 | —COCH₂NHCO(CH₂)₁₀CH₃ | —CO(CH₂)₁₀CH₃ | —CO(CH₂)₁₀CH₃ | —COCH₂NHCO(CH₂)₆CH₃ |
| 57 | —COCH₂NHCO(CH₂)₈CH₃ | —COCH₂NHCO(CH₂)₈CH₃ | —COCH₂NHCO(CH₂)₈CH₃ | —CO(CH₂)₁₂CH₃ |
| 58 | —COCH₂NHCO(CH₂)₁₀CH₃ | —CO(CH₂)₁₀CH₃ | —COCH₂NHCO(CH₂)₁₀CH₃ | —CO(CH₂)₁₀CH₃ |
| 59 | —COCH₂NHCO(CH₂)₁₀CH₃ | —CO(CH₂)₁₂CH₃ | —COCH₂NHCO(CH₂)₁₀CH₃ | —CO(CH₂)₂CO(CH₂)NHCO—(OH)₆CH₃ |
| 60 | —COCH₂NHCO(CH₂)₁₀CH₃ | —CO(CH₂)₁₂CH₃ | —COCH₂NHCO(CH₂)₁₀CH₃ | CH₃<br>—COCH₂NCO(CH₂)₆CH₃ |
| 61 | —CO(CH₂)₁₂CH₃ | —CO(CH₂)₁₂CH₃ | —COCH₂NHCO(CH₂)₁₀CH₃ | —COCH₂NHCO(CH₂)₆CH₃ |
| 62 | —CO(CH₂)₁₂CH₃ | —CO(CH₂)₅NHCO(CH₂)₆CH₃ | —COCH₂NHCO(CH₂)₁₀CH₃ | —COCH₂NHCO(CH₂)₆CH₃ |
| 63 | —COCH₂NHCO(CH₂)₁₀CH₃ | —CO(CH₂)₁₂CH₃ | —COCH₂NHCO(CH₂)₁₀CH₃ | —COCH₂NHCO(CH₂)₄CH₃ |
| 64 | —COCH₂NHCO(CH₂)₁₀CH₃ | —COCH₂NHCO(CH₂)₆CH₃ | —COCH₂NHCO(CH₂)₁₀CH₃ | —CO(CH₂)₁₂CH₃ |

-continued $$\text{(Ia)}$$

| Example No. | R⁴ | R³ | R² | R¹ |
|---|---|---|---|---|
| 65 | —CO(CH₂)₁₂CH₃ | —CO(CH₂)₁₂CH₃ | —COCH₂CH(OH)(CH₂)₁₀CH₃ | —COCH₂CH(OH)(CH₂)₁₀CH₃ |
| 66 | —CO(CH₂)₁₂CH₃ | —COCH₂CH(OH)(CH₂)₁₀CH₃ | —COCH₂CH(OH)(CH₂)₁₀CH₃ | —CO(CH₂)₁₂CH₃ |
| 67 | —COCH₂CH(OH)(CH₂)₁₀CH₃ | —CO(CH₂)₁₂CH₃ | —CO(CH₂)₁₂CH₃ | —COCH₂CH(OH)(CH₂)₁₀CH₃ |
| 68 | —COCH₂CH(OH)(CH₂)₁₀CH₃ | —COCH₂CH(OH)(CH₂)₁₀CH₃ | —COCH₂CH(OH)(CH₂)₁₀CH₃ | —COCH₂CH(OH)(CH₂)₁₀CH₃ |
| 69 | —CO(CH₂)₁₂CH₃ | —CO(CH₂)₁₂CH₃ | —CO(CH₂)₁₂CH₃ | —CO(CH₂)₁₂CH₃ |
| 70 | —CO(CH₂)₆CH₃ | —CO(CH₂)₆CH₃ | —CO(CH₂)₆CH₃ | —CO(CH₂)₆CH₃ |
| 71 | —CO(CH₂)₈CH₃ | —CO(CH₂)₈CH₃ | —CO(CH₂)₈CH₃ | —CO(CH₂)₈CH₃ |
| 72 | —CO(CH₂)₁₀CH₃ | —CO(CH₂)₁₀CH₃ | —CO(CH₂)₁₀CH₃ | —CO(CH₂)₁₀CH₃ |
| 73 | —CO(CH₂)₁₄CH₃ | —CO(CH₂)₁₄CH₃ | —CO(CH₂)₁₄CH₃ | —CO(CH₂)₁₄CH₃ |
| 74 | —COCH₂CH(OH)(CH₂)₁₀CH₃ | —COCH₂CH(OH)(CH₂)₁₀CH₃ | —CO(CH₂)₁₂CH₃ | —CO(CH₂)₁₂CH₃ |

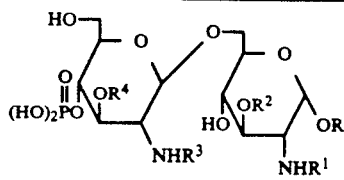

| Example No. | R⁴ | R³ | R² | R¹ | R |
|---|---|---|---|---|---|
| 75 | —COCH₂NHCO(CH₂)₁₀CH₃ | —CO(CH₂)₁₂CH₃ | —COCH₂NHCO(CH₂)₁₀CH₃ | —CO(CH₂)₁₂CH₃ | —CH(CH₂COOH)₂ |
| 76 | —CO(CH₂)₁₂CH₃ | —CO(CH₂)₁₂CH₃ | —CO(CH₂)₁₂CH₃ | —CO(CH₂)₁₂CH₃ | —CH(CH₂COOH)₂ |
| 77 | —CO(CH₂)₁₂CH₃ | —CO(CH₂)₁₂CH₃ | —CO(CH₂)₁₂CH₃ | —CO(CH₂)CH₃ | —CH₂COOH |

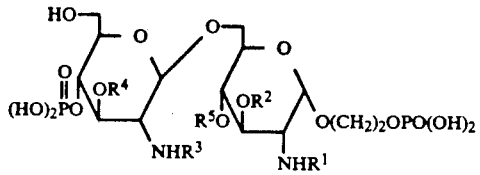

| Example No. | R⁴ | R³ | R⁵ | R² | R¹ |
|---|---|---|---|---|---|
| 78 | —CO(CH₂)₂CO(CH₂)₉CH₃ | —CO(CH₂)₁₂CH₃ | —COCOOH | —CO(CH₂)₂CO(CH₂)₉CH₃ | —CO(CH₂)₁₂CH₃ |
| 79 | —COCH₂NHCO(CH₂)₁₀CH₃ | —CO(CH₂)₁₂CH₃ | —PO(OH)₂ | —COCH₂NHCO(CH₂)₁₀CH₃ | —CO(CH₂)₁₂CH₃ |
| 80 | —COCH₂NHCO(CH₂)₁₀CH₃ | —CO(CH₂)₅NHCO(CH₂)₆CH₃ | —PO(OH)₂ | —COCH₂NHCO(CH₂)₁₀CH₃ | —CO(CH₂)₁₂CH₃ |
| 81 | —COCH₂NHCO(CH₂)₁₀CH₃ | —CO(CH₂)₅NHCO(CH₂)₆CH₃ | CH₂CO—<br>\|<br>CH₂COOH | —COCH₂NHCO(CH₂)₁₀CH₃ | —CO(CH₂)₁₂CH₃ |

Physical properties of the compounds of Examples 9 to 81 are as follows:

| Example No. | Physical Properties |
|---|---|
| 9 | Melting Point: 140–150° C. (colored and jelly-like)<br>$[\alpha]_D^{25}$: +13.3° (c = 0.6, chloroform:methanol = 3:1 (v/v))<br>IR $\nu_{max}^{KBR}$ cm⁻¹: 3400, 2930, 2855, 1750, 1660, 1560<br>NMR (CDCl₃-CD₃OD), δ(ppm): 0.90 (12H, t), 1.32 (s), 2.1–2.3 (8H, m), 5.10 (1H, t), 5.38 (1H, t) |
| 10 | Melting Point: 174–180° C. (colored and jelly-like)<br>$[\alpha]_D^{25}$: +11.8° (c = 0.7, chloroform:methanol = 1:1 (v/v))<br>IR $\nu_{max}^{KBr}$ cm⁻¹: 3425, 2930, 2854, 1745, 1675, 1470<br>NMR (CDCl₃-CD₃OD), δ(ppm): 0.89 (12H, t), 1.28 (s), 2.27 (2H, t), 2.4–2.8 (12H, m), 2.93 (2H, m) 4.81 (1H, m), 5.14 (1H, t), 5.32 (1H, m) |
| 11 | Melting Point: 159–167° C. (colored and jelly-like)<br>$[\alpha]_D^{25}$: +10.2° (c = 0.6, chloroform:methanol = 1:1 (v/v))<br>IR $\nu_{max}^{KBr}$ cm⁻¹: 3330, 2925, 2855, 1745, 1655, 1560 1470, 1025<br>NMR (CDCl₃-CD₃OD), δ(ppm): 0.89 (12H, t), 1.27 (s), 2.20 (6H, m), 2.46 (2H, t), 2.6–2.8 (4H, m), 3.25 (2H, m), 3.63 (1H, m), 3.71 (1H, m), 3.90 (8H, m), 4.18 (4H, m), 4.76 (1H, d), 5.13 (1H, t), 5.24 (5H, t) |
| 12 | Melting Point: 165–171° C. (colored and jelly-like)<br>$[\alpha]_D^{25}$: +9.0° (c = 0.6, chloroform:methanol = 1:1 (v/v))<br>IR $\nu_{max}^{KBr}$ cm⁻¹: 3320, 2925, 2855, 1710, 1645, 1555 1470<br>NMR (CDCl₃-CD₃OD), δ(ppm): 0.89 (12H, t), 1.27 (s), 2.17 (6H, m), 2.47 (4H, m), 2.60 (4H, m), 2.73 (4H, m), 4.25 (1H, q), 4.75 (1H, d), 5.12 (1H, t), 5.25 (1H, t) |
| 13 | Melting Point: 169–173° C. (colored and jelly-like)<br>$[\alpha]_D^{25}$: +16.4° (c = 0.7, chloroform:methanol = 3:1 (v/v))<br>IR $\nu_{max}^{KBr}$ cm⁻¹: 3425, 2925, 2855, 1735, 1645, 1555 NMR (CDCl₃-CD₃OD), δ(ppm): 0.90 (12H, t), 2.2–2.4 (10H, m), 3.18 (2H, t), 5.16 (1H, t), 5.36 (1H, t) |
| 14 | Melting Point: 161–165° C. (colored and jelly-like)<br>$[\alpha]_D^{25}$: +9.2° (c = 0.6, chloroform:methanol = 3:1 (v/v))<br>IR $\nu_{max}^{KBr}$ cm⁻¹: 3405, 2930, 2855, 1760, 1660, 1550<br>NMR (CDCl₃-CD₃OD), δ(ppm): 0.90 (12H, t), 2.2–2.5 (8H, m), 2.96 and 3.04 (total 6H, each s), 5.18 (1H, t), 5.34 (1H, t) |
| 15 | Melting Point: 144–147° C. (colored and jelly-like)<br>$[\alpha]_D^{25}$: −2.4° (c = 0.8, chloroform:methanol = 3:1 (v/v))<br>IR $\nu_{max}^{KBr}$ cm⁻¹: 3405, 2925, 2855, 1745, 1655, 1555<br>NMR (CDCl₃-CD₃OD), δ(ppm): 0.90 (12H, t), 2.1–2.5 (8H, m), 2.82 and 3.02 and 3.04 (total 6H, each s), 4.88 (1H, d), 5.16 (1H, t), 5.29 (1H, t) |
| 16 | Melting Point: 150–154° C. (colored and jelly-like)<br>$[\alpha]_D^{25}$: +16.8° (c = 0.6, chloroform:methanol = 3:1 (v/v))<br>IR $\nu_{max}^{KBr}$ cm⁻¹: 3450, 2930, 2860, 1745, 1675 1470<br>NMR (CDCl₃-CD₃OD), δ(ppm): 0.88 (12H, t), 1.26 (br), 2.3–2.8 (18H, m), 2.96 and 3.10 and 3.18 (total 6H, each s), 5.16 (1H, m), 5.34 (1H, m) |
| 17 | Melting Point: 190–193° C. (colored and jelly-like)<br>$[\alpha]_D^{25}$: −5.4° (c = 0.7, chloroform:methanol = 3:1 (v/v))<br>IR $\nu_{max}^{KBr}$ cm⁻¹: 3305, 2925, 2855, 1750, 1650<br>NMR (CDCl₃-CD₃OD), δ(ppm): 0.90 (12H, t), 2.1–2.4 (8H, m), 5.16 (1H, t), 5.38 (1H, t) |
| 18 | Melting Point: 175–177° C. (colored and jelly-like)<br>$[\alpha]_D^{25}$: −2.2° (c = 0.8, chloroform:methanol = 3:1 (v/v))<br>IR $\nu_{max}^{KBr}$ cm⁻¹: 3310, 2925, 2855, 1745, 1660, 1555<br>NMR (CDCl₃-CD₃OD), δ(ppm): 0.89 (12H, t), 2.1–2.4 8H, m), 5.18 (1H, t), 5.32 (1H, t) |
| 19 | Melting Point: 145–150° C. (colored and jelly-like) |

| Example No. | Physical Properties |
|---|---|
| | $[\alpha]_D^{25}$: +1.7° (c = 0.6, chloroform:methanol = 3:1 (v/v))<br>IR $\nu_{max}^{KBr}$ cm$^{-1}$: 3300, 2925, 2855, 1755, 1685, 1645 1555<br>NMR (CDCl$_3$-CD$_3$OD), δ(ppm): 0.90 (12H, t), 1.30 (s), 2.29 (4H, t), 2.48 (4H, t), 4.73 (1H, d), 4.84 (1H, d), 5.19 (1H, t), 5.32 (1H, t) |
| 20 | Melting Point: 165–168° C. (colored and jelly-like)<br>$[\alpha]_D^{25}$: +10.2° (c = 0.5, chloroform:methanol = 3:1 (v/v))<br>IR $\nu_{max}^{KBr}$ cm$^{-1}$: 3310, 2930, 2865, 1735, 1645, 1555<br>NMR (CDCl$_3$-CD$_3$OD), δ(ppm): 0.90 (12H, t-br), 1.30 (s), 2.20 (12H, t), 2.36 (4H, m), 3.19 (8H, t), 4.68 (1H, d), 4.79 (1H, d), 5.16 (1H, t), 5.24 1H, t) |
| 21 | Melting Point: 178–183° C. (colored and jelly-like)<br>$[\alpha]_D^{25}$: +16.8° (c = 0.5, chloroform:methanol = 3:1 (v/v))<br>IR $\nu_{max}^{KBr}$ cm$^{-1}$: 3315, 2925, 2855, 1735, 1660, 1570<br>NMR (CDCl$_3$-CD$_3$OD), δ(ppm): 0.88 (12H, t), 1.26 (s), 2.20 (8H, t), 5.18 (1H, t), 2.56 (4H, m), 5.30 (1H, t) |
| 22 | Melting Point: 151–160° C. (colored and jelly-like)<br>$[\alpha]_D^{25}$: +2.4° (c = 0.3, chloroform:methanol = 3:1 (v/v))<br>IR $\nu_{max}^{KBr}$ cm$^{-1}$: 3350, 2925, 2855, 1750, 1647, 1555<br>NMR (CDCl$_3$-CD$_3$OD), δ(ppm): 0.88 (12H, t), 1.26 (s), 2.2–2.7 (16H, m), 5.18 (1H, t), 5.30 (1H, t) |
| 23 | Melting Point: 160–164° C. (colored and jelly-like)<br>$[\alpha]_D^{25}$: +14.5° (c = 0.7, chloroform:methanol = 3:1 (v/v))<br>IR $\nu_{max}^{KBr}$ cm$^{-1}$: 3330, 2930, 2860, 1755, 1660, 1565<br>NMR (CDCl$_3$-CD$_3$OD), δ(ppm): 0.90 (12H, t), 1.32 (s), 2.1–2.3 (8H, m), 5.10 (1H, t), 5.38 (1H, t) |
| 24 | Melting Point: 168–174° C. (colored and jelly-like)<br>$[\alpha]_D^{25}$: +6.6° (c = 0.3, chloroform:methanol = 3:1 (v/v))<br>IR $\nu_{max}^{KBr}$ cm$^{-1}$: 3315, 2930, 2860, 1760, 1660, 1555<br>NMR (CDCl$_3$-CD$_3$OD), δ(ppm): 0.88 (12H, t), 1.26 (s), 2.1–2.8 (20H, m), 5.20 (1H, t), 5.34 (1H, t) |
| 25 | Melting Point: 160–170° C. (gradually colored and jelly-like)<br>$[\alpha]_D^{25}$: +21.7° (c = 0.6, chloroform:methanol = 3:1 (v/v))<br>IR $\nu_{max}^{KBr}$ cm$^{-1}$: 3450, 2930, 2860, 1760, 1675, 1470<br>NMR (CDCl$_3$-CD$_3$OD), δ(ppm): 0.90 (12H, t), 1.32 (s), 2.43 (8H, m), 2.96 and 3.08 and 3.16 (total 12H, each m, s, s), 4.87 (2H, m), 5.20 (1H, m), 5.47 (1H, m) |
| 26 | Melting Point: 166–170° C. (colored and jelly-like)<br>$[\alpha]_D^{25}$: +10.6° (c = 1.0, chloroform:methanol = 3:1 (v/v))<br>IR $\nu_{max}^{KBr}$ cm$^{-1}$: 3330, 2925, 2855, 1745, 1660, 1560<br>NMR (CDCl$_3$-CD$_3$OD), δ(ppm): 0.88 (12H, t), 1.26 (s), 2.1–2.4 (8H, m), 3.5–3.8 (4H, m), 3.94 (6H, m), 4.20 (4H, m), 4.79 (1H, d), 5.19 (1H, t), 5.25 (1H, t) |
| 27 | Melting Point: 160–162° C. (colored and jelly-like)<br>$[\alpha]_D^{25}$: +12.9° (c = 0.7, chloroform:methanol = 3:1 (v/v))<br>IR $\nu_{max}^{KBr}$ cm$^{-1}$: 3320, 2925, 2855, 1730, 1655, 1565<br>NMR (CDCl$_3$-CD$_3$OD), δ(ppm): 0.90 (12H, t), 2.18 (8H, m), 2.36 (4H, m), 3.20 (4H, m), 4.78 (1H, d), 5.2 (2H, m) |
| 28 | Melting Point: 162–165° C. (colored and jelly-like)<br>$[\alpha]_D^{25}$: +10.7° (c = 0.6, chloroform:methanol:water = 8:3:1 (v/v) lower layer)<br>IR $\nu_{max}^{KBr}$ cm$^{-1}$: 3315, 2925, 2860, 1760, 1645, 1555<br>NMR (CDCl$_3$-CD$_3$OD), δ(ppm): 0.90 (12H, t), 2.1–2.4 (12H, m), 3.1–3.3 (4H, t), 5.20 (1H, t), 5.37 (1H, t) |
| 29 | Melting Point: 160–164° C. (colored and jelly-like)<br>$[\alpha]_D^{25}$: +14.1° (c = 0.7, chloroform:methanol = 3:1 (v/v))<br>IR $\nu_{max}^{KBr}$ cm$^{-1}$: 3410, 2925, 2855, 1750, 1645, 1560<br>NMR (CDCl$_3$-CD$_3$OD), δ(ppm): 0.90 (12H, t), 2.1–2.4 (8H, m), 5.18 (1H, t), 5.38 (1H, t) |
| 30 | Melting Point: 165–168° C. (colored and jelly-like)<br>$[\alpha]_D^{25}$: +8.6° (c = 0.7, chloroform:methanol:water = 6:4:1 (v/v))<br>IR $\nu_{max}^{KBr}$ cm$^{-1}$: 3315, 3100, 2925, 2855, 1745, 1660, 1565<br>NMR (CDCl$_3$-CD$_3$OD), δ(ppm): 0.90 (12H, t), 2.2–2.5 (12H, m), 4.81 (1H, d), 5.19 (1H, t), 5.35 (1H, t) |
| 31 | Melting Point: 177–185° C. (gradually colored and jelly-like)<br>$[\alpha]_D^{25}$: +3.7° (c = 0.6, chloroform:methanol:water = 6:4:1 (v/v))<br>IR $\nu_{max}^{KBr}$ cm$^{-1}$: 3315, 2930, 2855, 1750, 1660, 1560<br>NMR (CDCl$_3$-CD$_3$OD), δ(ppm): 0.88 (12H, t), 1.26 (s), 2.1–2.5 (10H, m), 5.18 (1H, t), 5.34 (1H, t) |
| 32 | $[\alpha]_D^{25}$: +2.4° (chloroform:methanol:water:triethylamine = 8:3:0.5:0.01 (v/v))<br>NMR (CDCl$_3$-CD$_3$OD), δ(ppm): 0.90 (12H, t), 1.28 (s), 2.1–2.4 (8H, m), 5.16 (1H, t), 5.32 (1H, t) |
| 33 | Melting Point: 170–175° C. (colored and jelly-like)<br>$[\alpha]_D^{25}$: (c = 0.6, chloroform:methanol = 3:1 (v/v))<br>IR $\nu_{max}^{KBr}$ cm$^{-1}$: 3300, 2925, 2855, 1750, 1680, 1565<br>NMR (CDCl$_3$-CD$_3$OD), δ(ppm): 0.90 (12H, t), 1.30 (s), 2.2–2.5 (8H, m), 5.20 (1H, m), 5.37 (1H, m) |
| 34 | Melting Point: 182–185° C. (colored and jelly-like)<br>$[\alpha]_D^{25}$: +11.5° (c = 0.7, chloroform:methanol = 3:1 (v/v))<br>IR $\nu_{max}^{KBr}$ cm$^{-1}$: 3315, 2925, 2855, 1735, 1645, 1560<br>NMR (CDCl$_3$-CD$_3$OD), δ(ppm): 0.90 (12H, t), 2.1–2.4 (12H, m), 3.1–3.3 (4H, m), 5.1–5.4 (2H, m) |
| 35 | Melting Point: 157–162° C. (colored and jelly-like)<br>$[\alpha]_D^{25}$: +13.8° (c = 0.5, chloroform:methanol = 3:1 (v/v))<br>IR $\nu_{max}^{KBr}$ cm$^{-1}$: 3330, 2930, 2860, 1755, 1660, 1565<br>NMR (CDCl$_3$-CD$_3$OD), δ(ppm): 0.91 (12H, t), 1.32 (s), 2.1–2.3 (8H, m), 5.10 (1H, t), 5.38 (1H, t) |
| 36 | Melting Point: 168–172° C. (colored and jelly-like)<br>$[\alpha]_D^{25}$: +14.6. (c = 1.0, chloroform:methanol = 3:1 (v/v))<br>IR $\nu_{max}^{KBr}$ cm$^{-1}$: 3320, 2930, 2860, 1755, 1660, 1565<br>NMR (CDCl$_3$-CD$_3$OD), δ(ppm): 0.91 (12H, t), 1.32 (br), 2.12–2.32 (8H, m), 5.18 (1H, m), 5.36 (1H, m) |
| 37 | Melting Point: 175–180° C. (colored and jelly-like)<br>$[\alpha]_D^{25}$: +9.9° (c = 0.7, chloroform:methanol = 3:1 (v/v))<br>IR $\nu_{max}^{KBr}$ cm$^{-1}$: 3300, 2930, 2860, 1750, 1675, 1580 1560<br>NMR (CDCl$_3$-CD$_3$OD), δ(ppm): 0.89 (12H, t), 1.30 (s), 2.2–2.5 (8H, m), 2.95 and 3.12 (total 9H, each m), 4.85 (1H, d), 5.18 (1H, t), 5.35 (1H, m) |
| 38 | Melting Point: 170–175° C. (colored and jelly-like)<br>$[\alpha]_D^{25}$: +14.9° (c = 0.6, chloroform:methanol = 3:1 (v/v))<br>IR $\nu_{max}^{KBr}$ cm$^{-1}$: 3450, 3300, 2930, 2860, 1755, 1675<br>NMR (CDCl$_3$-CD$_3$OD), δ(ppm): 0.91 (12H, t), 1.32 (s), 2.29 (2H, m), 2.43 (6H, m), 2.94 and 3.12 (total 9H, each m), 4.83 (1H, d), 5.18 (1H, m), 5.44 (1H, m) |
| 39 | Melting Point: 166–174° C. (colored and jelly-like)<br>$[\alpha]_D^{25}$: +9.2° (c = 0.6, chloroform:methanol = 3:1 (v/v))<br>IR $\nu_{max}^{KBr}$ cm$^{-1}$: 3310, 2930, 2860, 1760, 1660, 1565<br>NMR (CDCl$_3$-CD$_3$OD), δ(ppm): 0.88 (12H, t), 1.26 (s), 2.1–2.4 (20H, m), 2.94 (3H, s), 3.04 (3H, s), 5.18 (1H, t), 5.36 (1H, t) |
| 40 | Melting Point: 170–186° C. (gradually colored and jelly-like)<br>$[\alpha]_D^{25}$: +7.8° (c = 1.1, chloroform:methanol = 3:1 (v/v))<br>IR $\nu_{max}^{KBr}$ cm$^{-1}$: 3310, 2930, 2860, 1750, 1660, 1565<br>NMR (CDCl$_3$-CD$_3$OD), δ(ppm): (12H, t), 1.26 (s), 2.20 (8H, t), 2.43 (4H, t), 2.94 (1H, m), 3.11 (6H, s), 3.19 (4H, m), 4.81 (1H, m), 5.19 (1H, t), 5.38 (1H, t) |
| 41 | Melting Point: 184–186° C. (colored and jelly-like)<br>$[\alpha]_D^{25}$: +6.0° (c = 0.5, chloroform:methanol = 3:1 (v/v))<br>IR $\nu_{max}^{KBr}$ cm$^{-1}$: 3460, 1758, 1662<br>NMR (CDCl$_3$-CD$_3$OD), δ(ppm): 0.88 (12H, t), 1.26 (s), 2.1–2.5 (8H, m), 2.94, 3.12 (total 6H, s), 4.80 (1H, m), 5.18 (1H, m), 5.38 (1H, m) |
| 42 | Melting Point: 155–165° C. (gradually colored and jelly-like)<br>$[\alpha]_D^{25}$: +8.2° (c = 0.7, chloroform:methanol:water = |

-continued

| Example No. | Physical Properties |
|---|---|
| | 6:4:1 (v/v))<br>IR $\nu_{max}^{KBr}$ cm$^{-1}$: 3320, 2930, 2850, 1760, 1645, 1565<br>NMR (CDCl$_3$-CD$_3$OD), δ(ppm): 0.90 (12H, t), 1.30 (s), 2.2 (12H, m), 3.18 (4H, t-br), 5.19 (1H, t), 5.36 (1H, t) |
| 43 | Melting Point: 165–168° C. (colored and jelly-like)<br>[α]$_D^{25}$: +23.6° (c = 0.6, chloroform:methanol = 3:1 (v/v))<br>IR $\nu_{max}^{KBr}$ cm$^{-1}$: 3450, 2925, 2855, 1735, 1675, 1635<br>NMR (CDCl$_3$-CD$_3$OD), δ(ppm): 0.90 (12H, t), 1.30 (s), 2.3–2.5 (8H, m), 2.92 and 2.94 and 3.07 and 3.09 (total 6H, s), 4.74 (1H, d), 4.87 (1H, d), 5.14 (1H, t), 5.38 (1H, t) |
| 44 | Melting Point: 177–179° C. (colored and jelly-like)<br>[α]$_D^{25}$: +11.7° (c = 0.7, chloroform:methanol = 3:1 (v/v))<br>IR $\nu_{max}^{KBr}$ cm$^{-1}$: 3310, 2860, 1734, 1659, 1560<br>NMR (CDCl$_3$-CD$_3$OD), δ(ppm): 0.90 (12H, t), 2.1–2 4 (12H, m), 3.10 (4H, t), 5.1–5.3 (2H, m) |
| 45 | Melting Point: 145–150° C. (colored and jelly-like)<br>[α]$_D^{25}$: +7.6° (c = 0.8, chloroform:methanol = 3:1 (v/v))<br>IR $\nu_{max}^{KBr}$ cm$^{-1}$: 3300, 1760, 1665, 1555<br>NMR (CDCl$_3$-CD$_3$OD), δ(ppm): 0.90 (12H, t), 1.30 (s), 2.30 (8H, m), 4.84 (1H, d), 5.19 (1H, t), 5.33 (1H, t) |
| 46 | Melting Point: 148–153° C. (colored and jelly-like)<br>[α]$_D^{25}$: +18.4° (c = 0.9, chloroform:methanol = 3:1 (v/v))<br>IR $\nu_{max}^{KBr}$ cm$^{-1}$: 3300, 1745, 1645, 1555<br>NMR (CDCl$_3$-CD$_3$OD), δ(ppm): 0.90 (12H, t), 1.30 (s), 2.30 (8H, m), 4.86 (1H, d), 5.16 (1H, t), 5.34 (1H, t) |
| 47 | Melting Point: 155–158° C. (colored and jelly-like)<br>[α]$_D^{25}$: +11.6° (c = 1 0, chloroform:methanol = 3:1 (v/v))<br>IR $\nu_{max}^{KBr}$ cm$^{-1}$: 3320, 1745, 1645, 1555<br>NMR (CDCl$_3$-CD$_3$OD), δ(ppm): 0.89 (12H, t), 1.30 (s), 2.1–2.4 (12H, m), 3.18 (4H, br), 4.67 (1H, d), 5.2 (2H, m) |
| 48 | NMR (CDCl$_3$-CD$_3$OD), δ(ppm): 0.88 (12H, t), 1.26 (s), 1.9–2.1 (4H, m), 2.2–2.4 (8H, m), 5.16 (1H, t), 5.30 (1H, m) |
| 49 | [α]$_D^{25}$: +4.3° (c = 0.8, chloroform:methanol = 3:1 (v/v))<br>NMR (CDCl$_3$-CD$_3$OD), δ(ppm): 0.88 (12H, t), 1.26 (s), 1.9–2.2 (4H, m), 2.2–2.4 (8H, m), 4.80 (1H, d), 5.14 (1H, t), 5.30 (1H, t) |
| 50 | [α]$_D^{25}$: +14.1° (c = 0.7, chloroform:methanol:water = 8:3:0.5 (v/v))<br>NMR (CDCl$_3$-CD$_3$OD), δ(ppm): 0.88 (6H, t), 1.26 (s), 1.4–1.8 (m), 2.08 (4H, m), 2.34 (4H, m), 4.63 (1H, d), 4.78 (1H, d), 5.20 (2H, m) |
| 51 | [α]$_D^{25}$: +16.6° (c = 1.0, chloroform:methanol:water = 8:3:0.5 (v/v))<br>NMR (CDCl$_3$-CD$_3$OD), δ(ppm): 0.88 (6H, t), 1.26 (s), 1.4–1.8 (m), 2.20 (4H, m), 2.36 (4H, m), 4.86 (1H, d), 5.14 (1H, t), 5.30 (1H, t) |
| 52 | Melting Point: 148–153° C. (colored and jelly-like)<br>[α]$_D^{25}$: +10.0° (c = 0.7, chloroform:methanol = 3:1 (v/v))<br>IR $\nu_{max}^{KBr}$ cm$^{-1}$: 3320, 2925, 2855, 1745, 1645, 1565<br>NMR (CDCl$_3$-CD$_3$OD), δ(ppm): 0.90 (12H, t), 1.30 (s), 2.2–2.3 (8H, m), 4.70 (1H, d), 4.81 (1H, d), 5.16 (1H, t), 5.31 (1H, t) |
| 53 | Melting Point: 135–138° C. (colored and jelly-like)<br>[α]$_D^{25}$: +13.3° (c = 0.1, chloroform:methanol = 3:1 (v/v))<br>IR $\nu_{max}^{KBr}$ cm$^{-1}$: 3405, 2925, 2855, 1720, 1660, 1555<br>NMR (CDCl$_3$-CD$_3$OD), δ(ppm): 0.88 (12H, t), 1.26 (br), 2.3–2.8 (24H, m), 5.16 (1H, m), 5.30 (1H, m) |
| 54 | Melting Point: 168–173° C. (colored and jelly-like)<br>[α]$_D^{25}$: +9.4° (c = 0.5, chloroform:methanol:water = 6:4:1 (v/v))<br>IR $\nu_{max}^{KBr}$ cm$^{-1}$: 3350, 2930, 1745, 1660, 1570<br>NMR (CDCl$_3$-CD$_3$OD), δ(ppm): 0.90 (12H, t), 1.30 (s), 2.1–2.3 (10H, m), 3.18 (2H, t), 4.78 (2H, m), 5.18 (1H; t), 5.35 (1H, m) |
| 55 | Melting Point: 182–188° C. (colored and jelly-like)<br>[α]$_D^{25}$: +11.8° (c = 0.7, chloroform:methanol = 1:1 (v/v))<br>IR $\nu_{max}^{KBr}$ cm$^{-1}$: 3310, 2926, 2854, 1749, 1677, 1563<br>NMR (CDCl$_3$-CD$_3$OD), δ(ppm): 0.89 (12H, t), 1.28 (s), 2.28 (4H, m), 2.4–2.8 (8H, m), 3.09, 3.13 (total 6H, each s), 3.6–4.3 (m), 4.82 (1H, d), 5.12 (1H, t), 5.34 (1H, t) |
| 56 | Melting Point: 160–165° C. (colored and jelly-like)<br>[α]$_D^{25}$: +16.8° (c = 0.5, chloroform:methanol = 3:1 (v/v))<br>IR $\nu_{max}^{KBr}$ cm$^{-1}$: 3330, 2925, 2855, 1735, 1645, 1550<br>NMR (CDCl$_3$-CD$_3$OD), δ(ppm): 0.89 (12H, t), 1.27 (s), 2.1–2.4 (10H, m), 3.16 (2H, t), 4.27 (1H, q), 4.76 (1H, d), 4.79 (1H, d), 5.12 (1H, dd), 5.33 (1H, t) |
| 57 | Melting Point: 158–162° C. (colored and jelly-like)<br>[α]$_D^{25}$: +13.0° (c = 0.4, chloroform:methanol = 3:1 (v/v))<br>IR $\nu_{max}^{KBr}$ cm$^{-1}$: 3328, 2926, 2854, 1749, 1659, 1563<br>NMR (CDCl$_3$-CD$_3$OD), δ(ppm): 0.89 (12H, t), 1.27 (s), 1.5–1.6 (8H, m), 2.1–2.3 (8H, m), 5.14 (1H, t), 5.32 (1H, t) |
| 58 | Melting Point: 168–172° C. (colored and jelly-like)<br>[α]$_D^{25}$: +14.2° (c = 0.6, chloroform:methanol = 3:1 (v/v))<br>IR $\nu_{max}^{KBr}$ cm$^{-1}$: 3320, 2925, 2855, 1750, 1660, 1565<br>NMR (CDCl$_3$-CD$_3$OD), δ(ppm): 0.81 (12H, t), 1.18 (s), 1.5–1.6 (8H, m), 2.0–2.2 (8H, m), 5.05 (1H, t), 5.23 (1H, t) |
| 59 | Melting Point: 184–187° C. (colored and jelly-like)<br>[α]$_D^{25}$: +15.4° (c = 0.6, chloroform:methanol = 1:1 (v/v))<br>IR $\nu_{max}^{KBr}$ cm$^{-1}$: 3430, 2930, 2855, 1755, 1660, 1565, 1470, 1385 |
| 60 | Melting Point: 178–182° C. (colored and jelly-like)<br>[α]$_D^{25}$: +9.5° (c = 0.6, chloroform:methanol = 1:1 (v/v))<br>IR $\nu_{max}^{KBr}$ cm$^{-1}$: 3405, 2930, 2855, 1760, 1660, 1555, 1470, 1205, 1025<br>NMR (CDCl$_3$-CD$_3$OD), δ(ppm): 0.89 (12H, t), 1.27 (s), 1.61 (m), 2.12–2.36 (10H, m), 2.91, 3.03 (total 3H, each s), 4.77 (1H, d), 5.14 (1H, t), 5.32 (1H, t) |
| 61 | Melting Point: 192–198° C. (colored and jelly-like)<br>[α]$_D^{25}$: +7.8° (c = 0.5, chloroform:methanol = 1:1 (v/v))<br>IR $\nu_{max}^{KBr}$ cm$^{-1}$: 3355, 2930, 2855, 1745, 1660, 1565, 1470, 1385, 1210<br>NMR (CDCl$_3$-CD$_3$OD), δ(ppm): 0.89 (12H, t), 1.28 (s), 1.60 (m), 2.12–2.38 (10H, m), 3.16 (2H, t), 3.53 (2H, m), 3.62 (1H, m), 3.72 (1H, m), 3.90 (8H, m), 4.16 (6H, m), 4.23 (1H, q), 4.59 (1H, d), 5.15 (1H, t), 5.21 (1H, t) |
| 62 | Melting Point: 194–195° C. (colored and jelly-like)<br>[α]$_D^{25}$: +7.2° (c = 0.8, chloroform:methanol = 1:1 (v/v))<br>IR $\nu_{max}^{KBr}$ cm$^{-1}$: 3320, 2930, 2855, 1745, 1660, 1555, 1025<br>NMR (CDCl$_3$-CD$_3$OD), δ(ppm): 0.89 (12H, t), 1.27 (s), 1.60 (m), 2.03–2.35 (12H, m), 3.16 (5H, m), 3.50 (2H, m), 3.54 (1H, m), 3.72 (1H, m), 3.88 (2H, m), 4.15 (5H, m), 4.27 (1H, q), 4.77 (1H, d), 5.15 (1H, t), 5.23 (1H, t) |
| 63 | Melting Point: 177–182° C. (colored and jelly-like)<br>[α]$_D^{25}$: +11.6° (c = 0.5, chloroform:methanol = 3:1 (v/v))<br>IR $\nu_{max}^{KBr}$ cm$^{-1}$: 3330, 2925, 2855, 1755, 1650, 1555, 1470<br>NMR (CDCl$_3$-CD$_3$OD), δ(ppm): 0.89 (12H, t), 1.27 (s), 2.13–2.27 (10H, m), 3.16 (2H, t), 4.74–4.77 (2H, t), 5.15 (1H, t), 5.32 (1H, t) |
| 64 | Melting Point: 173–177° C. (colored and jelly-like)<br>[α]$_D^{25}$: +9.5° (c = 0.5, chloroform:methanol:water = 6:4:1 (v/v))<br>IR $\nu_{max}^{KBr}$ cm$^{-1}$: 3330, 2925, 2855, 1755, 1660, 1565<br>NMR (CDCl$_3$-CD$_3$OD), δ(ppm): 0.89 (12H, t), 1.27 (s), 2.1–2.3 (10H, m), 3.17 (2H, m), 4.29 (1H, q), 4.75 (1H, d), 4.77 (1H, d), 5.14 (1H, dd), 5.33 (1H, dd) |
| 65 | NMR (CDCl$_3$-CD$_3$OD), δ(ppm): 0.90 (12H, t), 1.26 (s), 2.1–2.5 (8H, m), 4.83 (1H, d), 5.1–5.4 (2H, |

-continued

| Example No. | Physical Properties |
|---|---|
| 66 | Melting Point: 148–151° C. (colored and jelly-like)<br>NMR (CDCl$_3$-CD$_3$OD), δ(ppm): 0.90 (12H, t), 1.26 (s), 2.10–2.50 (8H, m), 4.82 (1H, d), 5.1–5.3 (2H, m) |
| 67 | Melting Point: 166.5–168.5° C. (gradually colored and jelly-like)<br>NMR (CDCl$_3$-CD$_3$OD), δ(ppm): 0.90 (12H, t), 1.26 (s), 2.16 (2H, t), 2.32 (4H, m), 2.50 (2H, d), 4.82 (1H, d), 5.16 (1H, t), 5.32 (1H, t) |
| 68 | Melting Point: 155–158° C. (colored and jelly-like)<br>[α]$_D^{25}$: +1.5° (c = 0.5, chloroform:methanol = 3:1 (v/v))<br>IR ν$_{max}^{KBr}$ cm$^{-1}$: 3400, 2930, 2860, 1740, 1660<br>NMR (CDCl$_3$-CD$_3$OD), δ(ppm): 0.90 (12H, t), 2.3–2.5 (8H, m), 5.2 (2H, m) |
| 69 | Melting Point: 153.5–155.0° C. (gradually brown-colored and jelly-like)<br>[α]$_D^{25}$: +13.3° (c = 0.6, chloroform:methanol = 9:1 (v/v))<br>IR ν$_{max}^{KBr}$ cm$^{-1}$: 3445, 2530, 1740, 1660, 1560<br>NMR (CDCl$_3$-CD$_3$OD), δ(ppm): 0.90 (12H), 2.10–2.26 (4H, m), 2.26–2.46 (4H, m) |
| 70 | Melting Point: 156–158.5° C. (gradually brown-colored and jelly-like)<br>[α]$_D^{25}$: +16.5° (c = 0.9, chloroform:methanol = 9:1 (v/v))<br>IR ν$_{max}^{KBr}$ cm$^{-1}$: 3450, 2930, 1735, 1660, 1560<br>NMR (CDCl$_3$-CD$_3$OD), δ(ppm): 0.89 (12H, t), 1.30 (s), 2.10–2.45 (8H, m), 5.20 (m) |
| 71 | Melting Point: 148–152° C. (gradually brown-colored and jelly-like)<br>[α]$_D^{25}$: +14.5° (c = 0.9, chloroform:methanol = 9:1 (v/v))<br>IR ν$_{max}^{KBr}$ cm$^{-1}$: 3450, 2930, 1745, 1650, 1560<br>NMR (CDCl$_3$-CD$_3$OD), δ(ppm): 0.90 (12H, t), 1.30 (s), 2.10–2.50 (8H, m), 5.10–5.35 (2H, m) |
| 72 | Melting Point: 156–158.5° C. (gradually brown-colored and jelly-like)<br>[α]$_D^{25}$: +14.1° (c = 0.9, chloroform:methanol = 9:1 (v/v))<br>IR ν$_{max}^{KBr}$ cm$^{-1}$: 3350, 2930, 1730, 1660, 1560<br>NMR (CDCl$_3$-CD$_3$OD), δ(ppm): 0.90 (12H, t), 1.30 (s), 2.1–2.5 (8H, m), 5.1–5.3 (2H, m) |
| 73 | Melting Point: 184–188° C. (gradually brown-colored and jelly-like)<br>[α]$_D^{25}$: +8.3° (c = 0.7, chloroform)<br>IR ν$_{max}^{KBr}$ cm$^{-1}$: 3455, 2925, 1745, 1665, 1555<br>NMR (CDCl$_3$-CD$_3$OD), δ(ppm): 0.89 (12H, t), 2.1–2.5 (8H, m), 5.1–5.4 (2H, m) |
| 74 | Melting Point: 169–171° C. (colored and jelly-like)<br>[α]$_D^{25}$: +6.2° (c = 1.22, chloroform:methanol = 3:1 (v/v))<br>NMR (CDCl$_3$-CD$_3$OD), δ(ppm): 0.90 (12H, t), 1.26 (s), 2.1–2.6 (8H, m), 4.80 (1H, d), 5.16 (1H, t), 5.34 (1H, t) |
| 75 | Melting Point: 140–145° C. (colored and jelly-like)<br>[α]$_D^{25}$: +10.3° (c = 0.6, chloroform:methanol = 3:1 (v/v))<br>IR ν$_{max}^{KBr}$ cm$^{-1}$: 3330, 2925, 2855, 1755, 1645, 1550<br>NMR (CDCl$_3$-CD$_3$OD), δ(ppm): 0.90 (12H, t), 1.30 (s), 2.1–2.3 (8H, m), 2.6–3.0 (4H, m), 4.89 (1H, d), 4.99 (1H, d), 5.09 (1H, t), 5.45 (1H, t) |
| 76 | Melting Point: 142–147° C. (colored and jelly-like)<br>[α]$_D^{25}$: +11.7° (c = 0.7, chloroform:methanol = 3:1 (v/v))<br>NMR (CDCl$_3$-CD$_3$OD), δ(ppm): 0.90 (12H, t), 1.30 (s), 2.1–2.4 (8H, m), 5.10 (1H, t), 5.30 (1H, t) |
| 77 | Melting Point: 145–148° C. (colored and jelly-like)<br>[α]$_D^{25}$: +14.2° (c = 0.5, chloroform:methanol = 3:1 (v/v))<br>IR ν$_{max}^{KBr}$ cm$^{-1}$: 3450, 2925, 2855, 1740, 1640<br>NMR (CDCl$_3$-CD$_3$OD), δ(ppm): 0.90 (12H, t, J = 6 Hz), 2.1–2.4 (8H, m), 4.80 (1H, d, J = 4 Hz), 5.24 (2H, m) |
| 78 | Melting Point: 149–153° C. (colored and jelly-like)<br>[α]$_D^{25}$: +20.6° (c = 0.31, chloroform:methanol = 1:1 (v/v))<br>IR ν$_{max}^{KBr}$ cm$^{-1}$: 3406, 2926, 2854, 1746, 1662, 1557<br>NMR (CDCl$_3$-CD$_3$OD), δ(ppm): 0.89 (12H, t), 1.27 (s), 2.23 (4H, m), 2.46 (6H, m), 2.59 (3H, m), 2.68 (3H, m), 4.89 (1H, d), 5.16 (1H, t), 5.25 (1H, t), 5.38 (1H, t) |
| 79 | Melting Point: 170–175° C. (colored and jelly-like)<br>[α]$_D^{25}$: +12.6° (c = 0.5, chloroform:methanol:water = 6:4:1 (v/v))<br>IR ν$_{max}^{KBr}$ cm$^{-1}$: 3320, 2925, 2855, 1755, 1660, 1560<br>NMR (CDCl$_3$-CD$_3$OD), δ(ppm): 0.89 (12H, t), 1.27 (s), 2.1–2.3 (8H, m), 3.18 (4H, m), 4.72 (1H, d), 5.23 (1H, t), 5.33 (1H, dd) |
| 80 | Melting Point: 172–175° C. (colored and jelly-like)<br>[α]$_D^{25}$: +12.6° (c = 0.5, chloroform:methanol:water = 6:4:1 (v/v))<br>IR ν$_{max}^{KBr}$ cm$^{-1}$: 3320, 2920, 2850, 1755, 1655, 1550<br>NMR (CDCl$_3$-CD$_3$OD), δ(ppm): 0.89 (12H, t), 1.27 (s), 2.1–2.3 (10H, m), 3.16 (2H, m), 4.28 (1H, q), 4.35 (1H, q), 4.69 (1H, d), 4.80 (1H, d), 5.21 (1H, t), 5.32 (1H, t) |
| 81 | Melting Point: 170–175° C. (colored and jelly-like)<br>[α]$_D^{25}$: +20.2° (c = 0.5, chloroform:methanol = 3:1 (v/v))<br>IR ν$_{max}^{KBr}$ cm$^{-1}$: 3330, 2930, 2855, 1755, 1655, 1555, 1470<br>NMR (CDCl$_3$-CD$_3$OD), δ(ppm): 0.89 (12H, t), 2.15–2.3 (10H, m), 2.6–2.7 (4H, m), 3.17 (2H, m), 4.58 (1H, d), 4.83 (1H, d), 5.07 (1H, t), 5.23 (1H, t), 5.30 (1H, t) |

TEST EXAMPLE

Fibrosarcoma cells (Meth A) ($2 \times 10^5$) induced in a BALB/c mouse by methyl chlolanthrene were intracutaneously implanted into the flank of seven BALB/c mice per group. A triethylamine salt of each of the compounds according to the present invention as shown in Table 1 below was dissolved or suspended in a 0.1% (v/v) triethylamine aqueous solution to prepare a 500 μg/ml solution or suspension. The solution or suspension was administered to the mice at a dose level of 100 μg/mouse through the tail vein on the 7th, 12th, and 21st days from the implantation.

The antitumor effect (%) on growth of the fibrosarcoma was determined by dividing the average tumor weight of the test group on the 21st day by the average tumor weight of the control group (non-treated group) and multiplying the quotient by 100.

For comparison, the same evaluation was made by using Compound A as a comparative compound. The results obtained are shown in Table 1.

TABLE 1

| Compound of Example | Antitumor Effect (%) |
|---|---|
| 1 | 19 |
| 2 | 13 |
| 3 | 5 |
| 9 | 9 |
| 26 | 11 |
| 33 | 24 |
| 44 | 7 |
| 47 | 8 |
| 54 | 6 |
| Compound A | 15 |
| Control | 100 |

It can be seen from Table 1 that the compounds according to the present invention exhibit antitumor activity equal or higher than Compound A.

TEST EXAMPLE 2

A triethylamine salt of each of the compounds according to the present invention as shown in Table 2 below was dissolved or suspended in a 5% (w/v) glucose aqueous solution containing 0.1 (v/v) triethylamine to prepare a 100 μg/ml solution or suspension. The solution or suspension was administered to three NZW male rabbits per group at a dose level of 50 μg/kg-b.w. through the ear vein for three consecutive days. The toxicity was evaluated by the number of dead animals after 24 hours from the final administration/the number of test animals. For comparison, Compound A was administered at a level of 5 μg/kg-b.w. The results obtained are shown in Table 2.

TABLE 2

| Compound of Example | Dose Level (μg/kg) | Number of Dead Rabbits/ Number of Test Animals |
| --- | --- | --- |
| 1 | 50 | 0/3 |
| 9 | 50 | 0/3 |
| 26 | 50 | 0/3 |
| 33 | 50 | 0/3 |
| 47 | 50 | 0/3 |
| Compound A | 5 | 4/4 |

As is apparent from Table 2, the compounds according to the present invention have toxicity lower than 1/10 of that of Compound A and thus prove excellent in safety.

While the invention has been described in detail and with reference to specific embodiments thereof, it will be apparent to one skilled in the art that various changes and modifications can be made therein without departing from the spirit and scope thereof.

What is claimed is:

1. A compound of the formula (III):

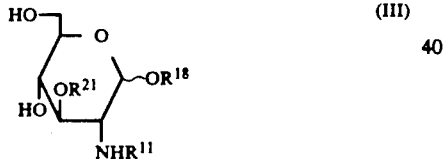

wherein $R^{11}$ and $R^{21}$ each represents —$COR^{71}$, —$COZ^3R^{81}$,

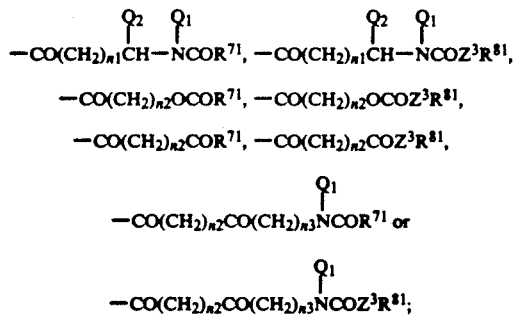

wherein $R^{71}$ represents an alkyl group having from 1 to 30 carbon atoms which may be substituted with one or more hydroxyl groups protected with a hydroxyl-protective group; $R^{81}$ represents a cycloalkyl group having from 3 to 12 carbon atoms which may be substituted with one or more hydroxyl groups protected with a hydroxyl-protective group; $Z^3$ represents an alkylene group having from 1 to 9 carbon atoms; $Q_1$ represents a hydrogen atom or an alkyl group having from 1 to 20 carbon atoms; $Q_2$ represents a hydrogen atom, an alkyl group having from 1 to 6 carbon atoms, —$CONH_2$, —$COOR^{16}$, or —$CH_2$—$O$—$R^{91}$, wherein $R^{16}$ represents a carboxyl-protective group which can be removed by catalytic reduction and $R^{91}$ represents a hydroxyl-protective group which can be removed by catalytic reduction; $R^{18}$ represents $ZCOOR^{14}$, $ZOPO(OR^{13})_2$,

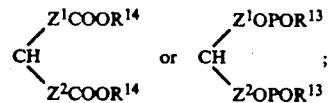

wherein $R^{13}$ represents a phosphono protective group which can be removed by catalytic reduction; $R^{14}$ represents a carboxyl protective group which can be removed by catalytic reduction; Z, $Z^1$ and $Z^2$ each represents an alkylene group having from 1 to 6 carbon atoms; n1 represents 0 or an integer of from 1 to 10; and n2 and n3 each represents an integer of from 1 to 20.

2. A compound as claimed in claim 1, wherein
$R^{18}$ is 1,3-di(benzyloxycarbonyl)isopropyl,
$R^{11}$ is tetradecanoyl, and
$R^{21}$ is N-dodecanoylglycyl.

3. A compound as claimed in claim 1, wherein
$R^{18}$ is 2-(diphenylphosphonoxy)ethyl,
$R^{11}$ is tetradecanoyl, and
$R^{21}$ is N-dodecanoylglycyl.

4. A compound as claimed in claim 1, wherein
$R^{18}$ is 2-(diphenylphosphonoxy)ethyl,
$R^{11}$ is tetradecanoyl, and
$R^{21}$ is N-dodecanoylglycyl.

5. A compound as claimed in claim 1, wherein
$R^{18}$ is 2-(diphenylphosphonoxy)ethyl,
$R^{11}$ is N-dodecanoyl-N-methylglycyl, and
$R^{21}$ is N-dodecanoylglycyl.

6. A compound as claimed in claim 1, wherein
$R^{18}$ is 2-(diphenylphosphonoxy)ethyl,
$R^{11}$ is 3-benzyloxytetradecanoyl, and
$R^{21}$ is 3-benzyloxytetradecanoyl.

7. A compound as claimed in claim 1, wherein
$R^{18}$ is benzyloxycarbonylmethyl,
$R^{11}$ is tetradecanoyl, and
$R^{21}$ is N-dodecanoylglycyl.

8. A compound as claimed in claim 1, wherein
$R^{18}$ is 1,3-di(benzyloxycarbonyl)isopropyl,
$R^{11}$ is tetradecanoyl, and
$R^{21}$ is N-dodecanoylglycyl.

9. A compound as claimed in claim 1, wherein
$R^{18}$ is 2-(diphenylphosphonoxy)ethyl,
$R^{11}$ is 6-octanoylaminohexanoyl, and
$R^{21}$ is tetradecanoyl.

10. A compound as claimed in claim 1, wherein
$R^{18}$ is 1,3-di(benzyloxycarbonyl)isopropyl,
$R^{11}$ is N-dodecanoyl-N-methylglycyl, and
$R^{21}$ is N-dodecanoylglycyl.

11. A compound as claimed in claim 1, wherein
$R^{18}$ is 2-(diphenylphosphonoxy)ethyl,
$R^{11}$ is 8-hexanoylaminooctanoyl, and
$R^{21}$ is tetradecanoyl.

12. A compound as claimed in claim 1, wherein
$R^{18}$ is 2-(diphenylphosphonoxy)ethyl,
$R^{11}$ is 6-octanoylaminohexanoyl, and
$R^{21}$ is N-dodecanoylglycyl.

13. A compound as claimed in claim 1, wherein
$R^{18}$ is 1,3-di(benzyloxycarbonyl)isopropyl,
$R^{11}$ is tetradecanoyl, and
$R^{21}$ is decanoylglycyl.

14. A compound as claimed in claim 1, wherein
$R^{18}$ is 2-(diphenylphosphonoxy)ethyl,
$R^{11}$ is 12-(acetamido)dodecanoyl, and
$R^{21}$ is tetradecanoyl.

15. A compound as claimed in claim 1, wherein
$R^{18}$ is 2-(diphenylphosphonoxy)ethyl,
$R^{11}$ is 6-(N-methyl-N-octanoylamino)hexanoyl, and
$R^{21}$ is N-dodecanoylglycyl.

* * * * *